(12) United States Patent
Wiley et al.

(10) Patent No.: US 12,064,533 B2
(45) Date of Patent: Aug. 20, 2024

(54) SYNTHETIC HYDROGEL COMPOSITE

(71) Applicant: Duke University, Durham, NC (US)

(72) Inventors: Benjamin J. Wiley, Durham, NC (US);
Huayu Tong, Durham, NC (US);
Jiacheng Zhao, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/324,951

(22) Filed: May 26, 2023

(65) Prior Publication Data

US 2023/0381376 A1    Nov. 30, 2023

Related U.S. Application Data

(62) Division of application No. 17/845,881, filed on Jun. 21, 2022, now Pat. No. 11,701,452.

(60) Provisional application No. 63/338,439, filed on May 4, 2022.

(51) Int. Cl.
    *A61L 27/48*    (2006.01)
    *A61F 2/30*     (2006.01)
    *A61L 27/52*    (2006.01)

(52) U.S. Cl.
    CPC .......... *A61L 27/48* (2013.01); *A61F 2/30756* (2013.01); *A61F 2/3094* (2013.01); *A61L 27/52* (2013.01); *A61F 2002/30024* (2013.01); *A61F 2002/30471* (2013.01); *A61F 2002/30761* (2013.01); *A61L 2400/12* (2013.01); *A61L 2430/06* (2013.01)

(58) Field of Classification Search
    None
    See application file for complete search history.

(56) References Cited

U.S. PATENT DOCUMENTS

| | | | |
|---|---|---|---|
| 5,514,378 A * | 5/1996 | Mikos | B01D 67/003 |
| | | | 521/27 |
| 5,632,745 A | 5/1997 | Schwartz | |
| 6,371,958 B1 | 4/2002 | Overaker | |
| 8,025,696 B2 | 9/2011 | Osada et al. | |
| 8,431,226 B2 | 4/2013 | Huerta et al. | |
| 8,679,190 B2 | 3/2014 | Myung et al. | |
| 11,701,452 B2 | 7/2023 | Wiley et al. | |
| 11,707,555 B2 | 7/2023 | Wiley et al. | |
| 2001/0010023 A1 | 7/2001 | Schwartz et al. | |

(Continued)

FOREIGN PATENT DOCUMENTS

| | | |
|---|---|---|
| CN | 1279997 C | 10/2006 |
| CN | 104208759 A | 12/2014 |

(Continued)

OTHER PUBLICATIONS

Nakayama et al.; High mechanical strength double-network hydrogel with bacterial cellulose; Advanced Functional Materials; 14(11); pp. 1124-1128; Nov. 2004.

(Continued)

*Primary Examiner* — Javier G Blanco
(74) *Attorney, Agent, or Firm* — Shay Glenn LLP

(57) ABSTRACT

Cellulose-reinforced hydrogels may include a cellulose nanofiber network and an interstitial hydrogel portion within interstitial regions of the cellulose nanofiber network, the interstitial hydrogel portion comprising polyvinyl alcohol (PVA), wherein the hydrogel component has a crystallinity of 20% or greater.

8 Claims, 21 Drawing Sheets

(56) References Cited

U.S. PATENT DOCUMENTS

| | | |
|---|---|---|
| 2004/0101518 A1 | 5/2004 | Vacanti et al. |
| 2005/0287187 A1 | 12/2005 | Mansmann |
| 2008/0133018 A1* | 6/2008 | Salovey ............. B29C 71/0063 623/18.11 |
| 2008/0241214 A1 | 10/2008 | Myung et al. |
| 2009/0252800 A1* | 10/2009 | Wan ........................ C12P 19/04 424/488 |
| 2011/0054622 A1 | 3/2011 | Muratoglu et al. |
| 2012/0265300 A1 | 10/2012 | Mauck et al. |
| 2013/0274892 A1 | 10/2013 | Lelkes et al. |
| 2014/0324169 A1 | 10/2014 | Maher et al. |
| 2016/0287392 A1 | 10/2016 | Patrick et al. |
| 2018/0291158 A1 | 10/2018 | Muratoglu et al. |
| 2019/0358365 A1 | 11/2019 | Vaughn |
| 2020/0390933 A1 | 12/2020 | Williams et al. |
| 2021/0085602 A1 | 3/2021 | Nuopponen et al. |
| 2021/0369915 A1 | 12/2021 | Wiley et al. |
| 2022/0354995 A1 | 11/2022 | Wiley et al. |
| 2023/0302205 A1 | 9/2023 | Wiley et al. |

FOREIGN PATENT DOCUMENTS

| | | | |
|---|---|---|---|
| CN | 104466140 A | 3/2015 | |
| CN | 108601644 A | 9/2018 | |
| CN | 208756338 U | 4/2019 | |
| CN | 208758338 U | 4/2019 | |
| CN | 109789020 A | 5/2019 | |
| CN | 110172126 B | 9/2020 | |
| DE | 102009024133 A1 | 12/2010 | |
| JP | H06-339490 A | 12/1994 | |
| JP | 2010524567 A | 7/2010 | |
| JP | 2014506177 A | 3/2014 | |
| WO | WO2006/013612 A1 | 2/2006 | |
| WO | WO2009/036431 A1 | 3/2009 | |
| WO | WO-2017031167 A1 * | 2/2017 | ............ A61F 2/0063 |
| WO | WO-2017096203 A1 * | 6/2017 | ............ A61L 27/16 |
| WO | WO2018/204315 A1 | 11/2018 | |
| WO | WO-2019094426 A1 * | 5/2019 | ......... A61F 2/30756 |
| WO | WO-2021067145 A1 * | 4/2021 | ............ A61L 27/20 |
| WO | WO2022/235741 A1 | 11/2022 | |
| WO | WO2023/215841 A2 | 11/2023 | |

OTHER PUBLICATIONS

Yang et al.; A synthetic hydrogel composite with the mechanical behavior and durability of cartilage; Advanced Functional Materials; 30(36); doi 10.1002/adfm.20033451; 23 pages; (Author Manuscript); Sep. 2020.

Xinmeng; Construction of nanocellulose three-dimensional networks in polylactic acid and its influence on the foaming process; (Disseration); retrived from the internet (https://wap.cnki.net/lunwen-1018132147.nh.html) 5 pages; on Jun. 16, 2022.

Zhoa et al.; High strength attachment through nanofibrous reinforcement; Advanced Healthcare Materials; 10(4); doi: 10.1002/adhm.2001119; 7 pages; Feb. 2021.

Wiley et al.; U.S. Appl. No. 18/559,337 entitled "Hydrogel-coated orthopedic implants," filed Nov. 6, 2023.

\* cited by examiner

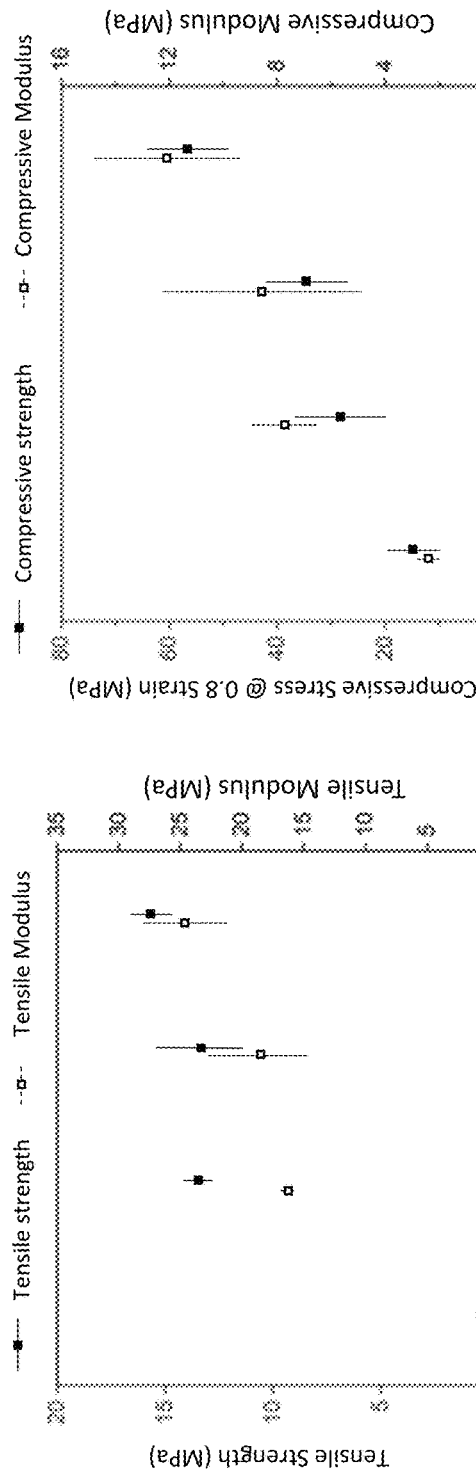
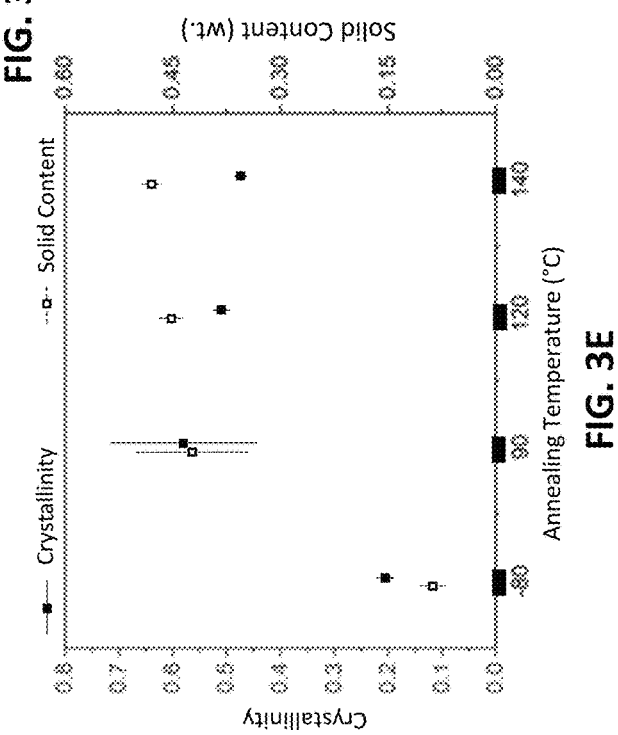

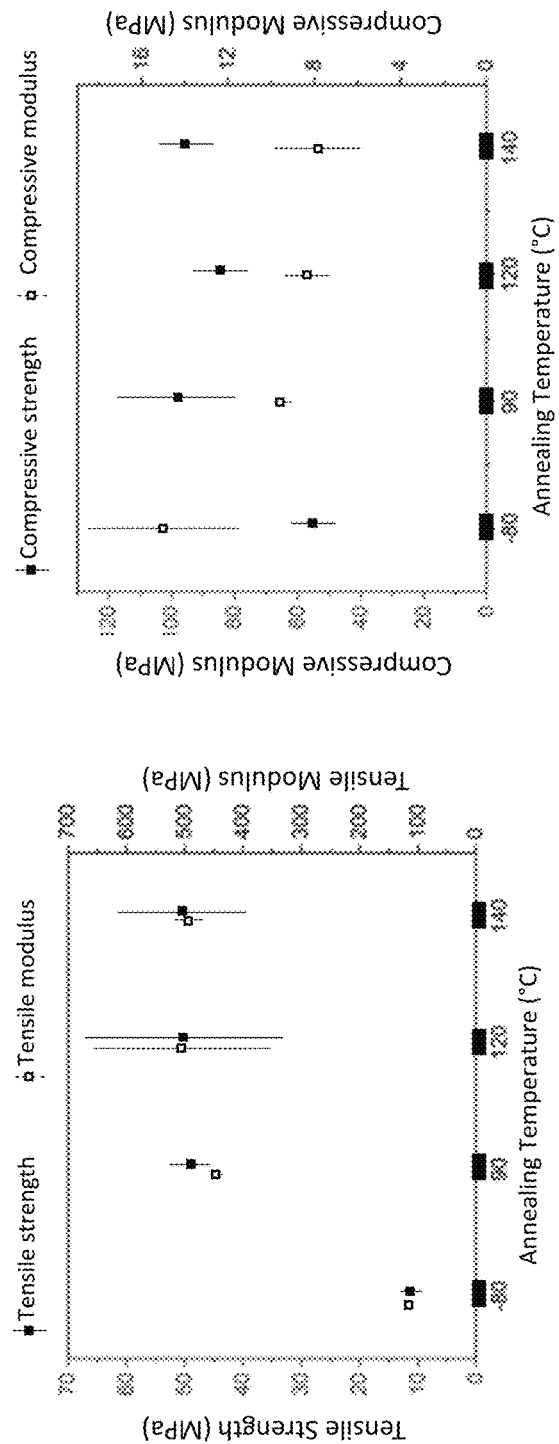
FIG. 4C
FIG. 4D
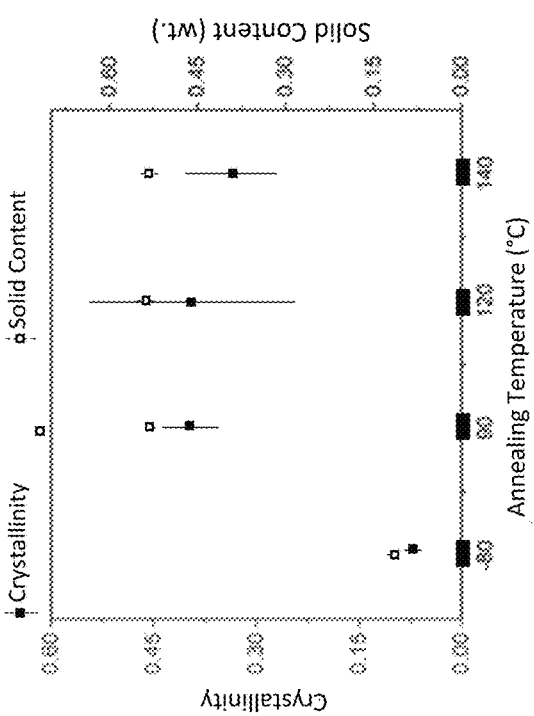
FIG. 4E

Pig Cartilage

BC-PVA-PAMPS

BC-PVA

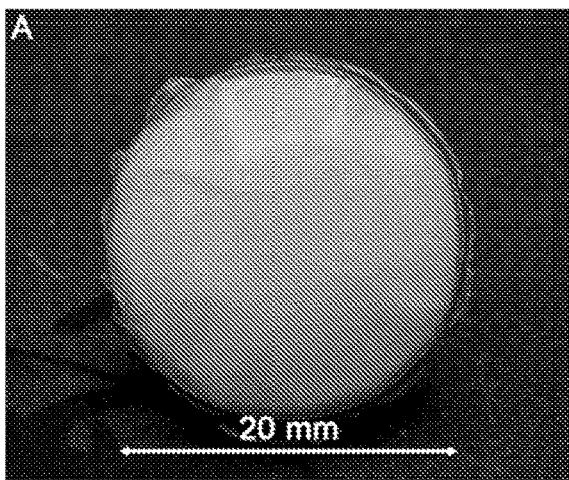
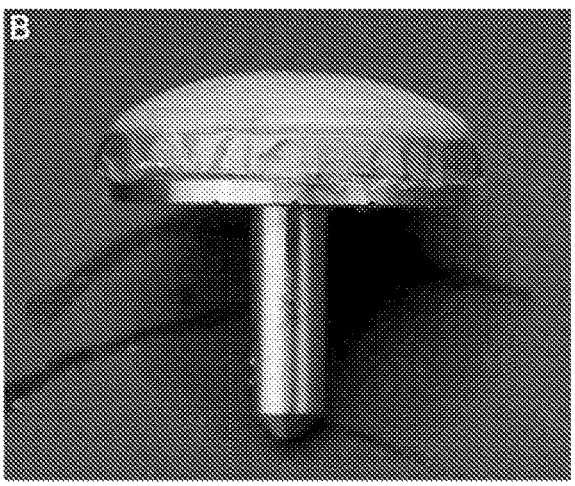
Before Mechanical Test
FIG. 9A  FIG. 9B
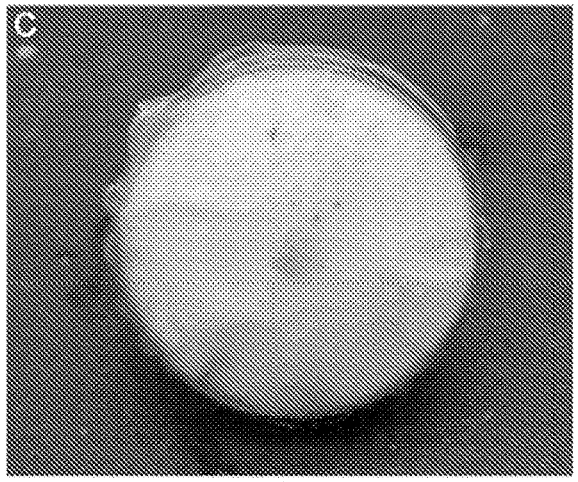
After Compression at 16 MPa. No Failure is Apparent
FIG. 9C  FIG. 9D
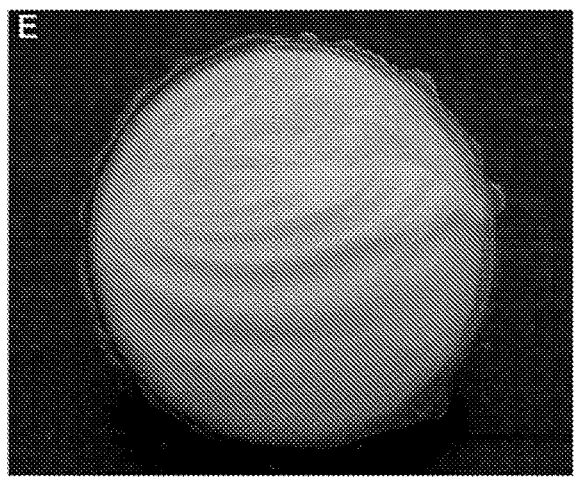
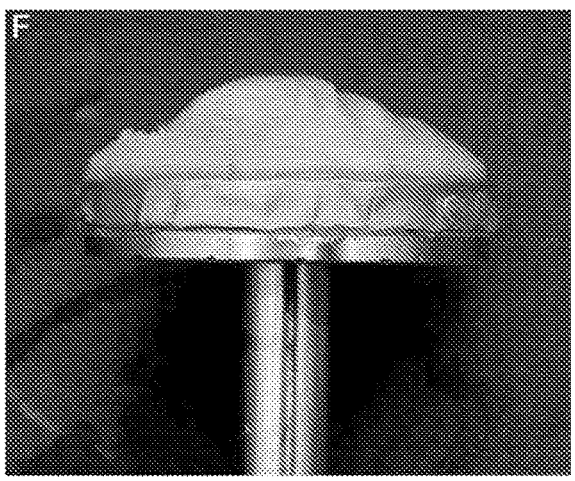
After Failure Under a Shear Stress of 0.9 MPa.
FIG. 9E  FIG. 9F

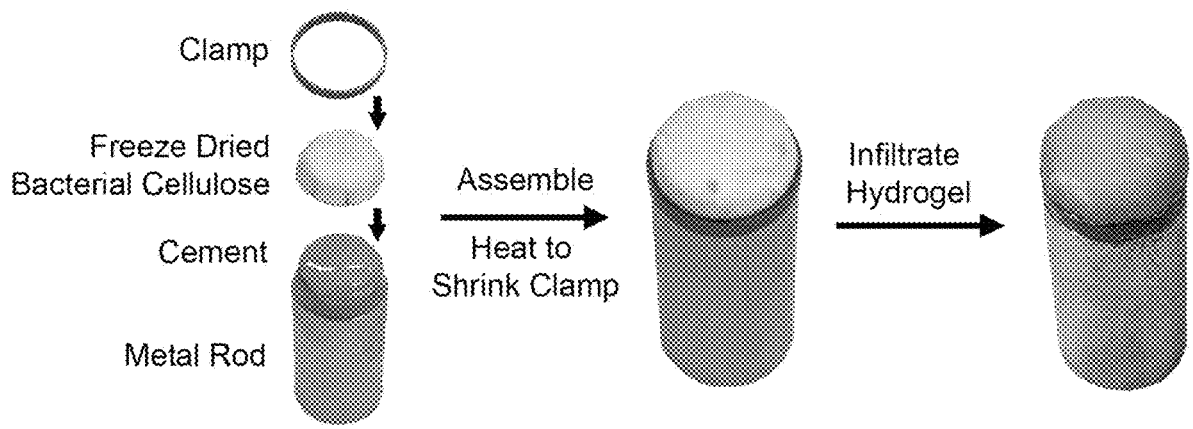
FIG. 12A
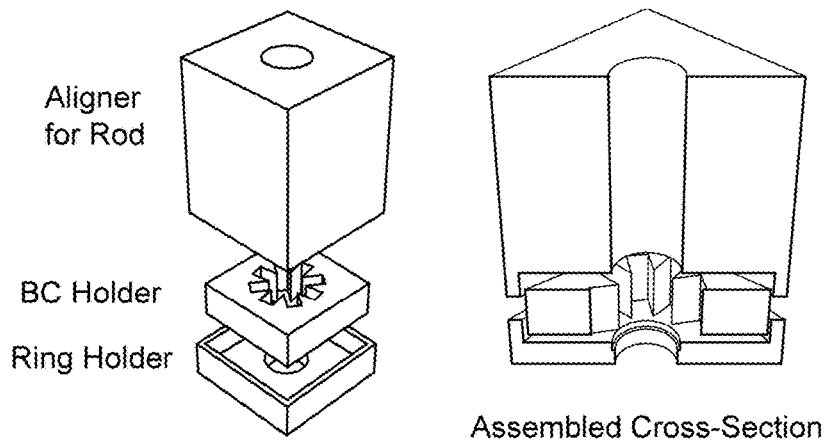
FIG. 12B
FIG. 12C
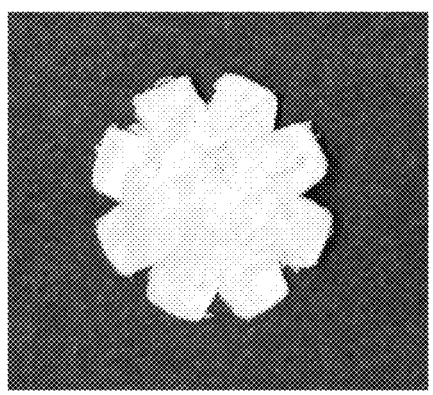
FIG. 12D
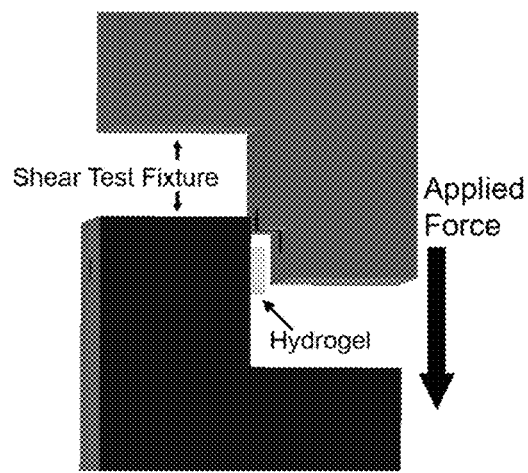
FIG. 13

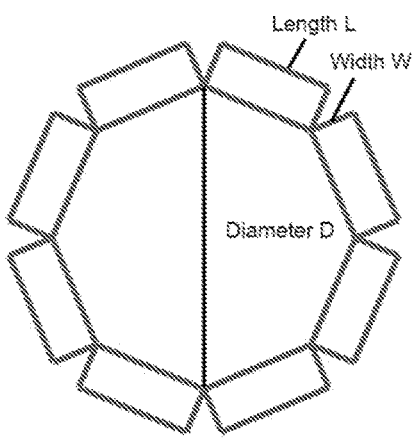
FIG. 12E
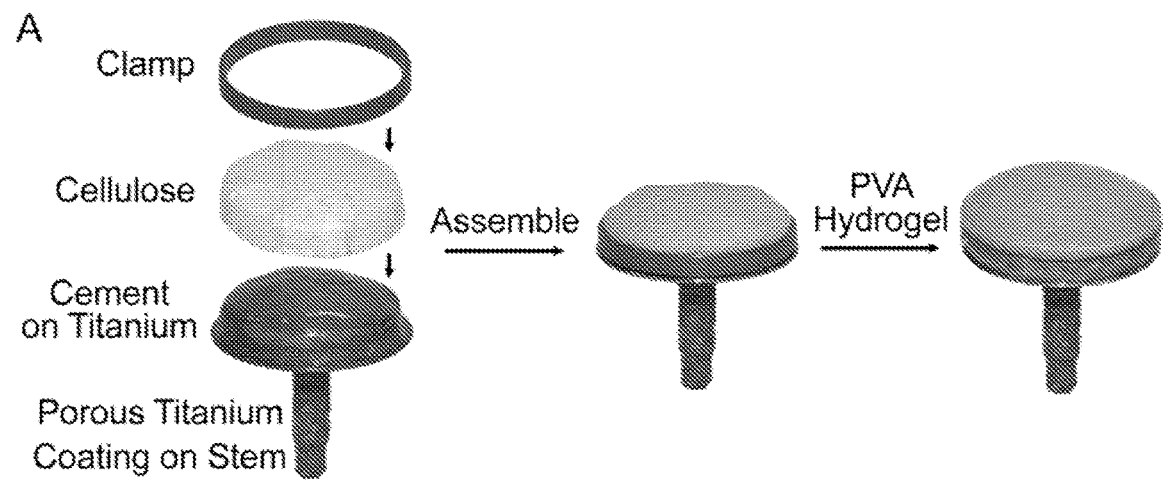
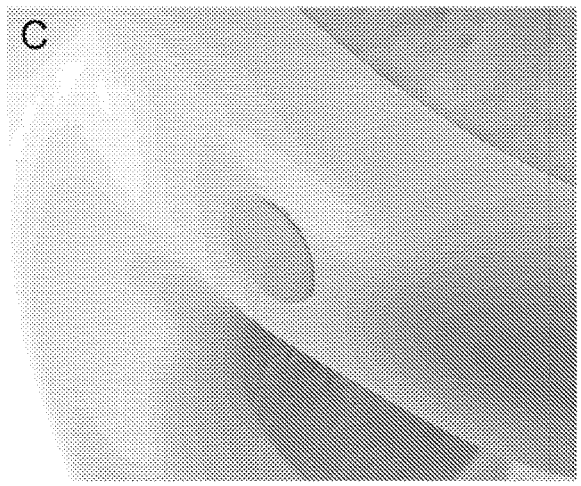
FIGS. 14A-14C

SYNTHETIC HYDROGEL COMPOSITE

CLAIM OF PRIORITY

This patent application is a divisional of U.S. patent application Ser. No. 17/845,881, filed Jun. 21, 2022, titled "SYNTHETIC HYDROGEL COMPOSITE," which claims priority to U.S. Provisional Patent Application No. 63/338,439, filed on May 4, 2022, titled "SYNTHETIC HYDROGEL COMPOSITE," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Every year, approximately 900,000 people in the United States suffer from damage to the articular cartilage that lines the ends of the bones. Osteoarthritis (OA) is an example of a degenerative joint disease that is a common cause of disability. Articular cartilage lesions most commonly occur in the knee and can cause debilitating pain. Cartilage lacks blood vessels and has a very limited capacity for healing. One approach to treating cartilage lesions is to attempt to regrow cartilage with a technique such as microfracture or autologous chondrocyte implantation. Unfortunately, these methods have high failure rates, prolonged rehabilitation times, and show decreasing efficacy in older patients. Implantation of fresh osteochondral allografts can speed recovery as they eliminate the need to regrow cartilage and. Unfortunately, the small supply of fresh allografts limits the number of these procedures. Failure of these treatment strategies usually leads to more invasive total knee replacement. While total knee replacement may be successful in older patients, it may not be suitable for younger patients for whom the implant is likely to fail within their lifetime, thus requiring a second invasive surgery. Thus, there is a clear need for minimally invasive treatment options that treat cartilage lesions with a low failure rate, enable rapid recovery, and are widely available.

Given the need for a less invasive alternative to total knee replacement for treatment of OA, there are ongoing efforts to replace damaged cartilage with a device made of traditional orthopedic materials, such as a cobalt-chrome alloy or ultra-high-molecular-weight polyethylene. However, these materials have a much higher coefficient of friction (COF) than cartilage and may cause an unacceptable level of wear on the opposing cartilage surface. In addition, these materials are much stiffer than cartilage and may therefore cause an abnormal stress distribution in the joint, potentially contributing to the damage of surrounding cartilage.

Hydrogels, polymer networks swollen with water, are a promising synthetic material for replacement of cartilage because hydrogels can be made to have similar mechanical and tribological properties as natural cartilage. However, there is a need to improve the physical properties hydrogels to withstand the wear and tear that an implant may encounter. For example, there is a need for hydrogels to be at the higher end of the range of strengths reported for cartilage while having a similar modulus, coefficient of friction, and resistance to wear as cartilage. Described herein are methods, hydrogel compositions, and apparatuses (e.g., implants) that may address these needs.

SUMMARY OF THE DISCLOSURE

This disclosure relates generally to artificial cartilage materials in implants suitable for repair of cartilage, including hydrogel composites and methods and for attaching a hydrogel composite to a surface of an implant.

Described herein are hydrogel materials for use as artificial cartilage in implants. A hydrogel may be infused in a nanofibrous material (e.g., a nanofiber network) and bound to a surface of an implant, such as a porous base. The composite hydrogel has physical properties, such as strength, modulus and wear resistance, and coefficient of friction (COF) that approximates or exceeds that of healthy cartilage bound to bone. The methods may involve a strengthening process to increase the crystallinity and decrease the water content of the hydrogel, thereby improving its mechanical properties for implementation as cartilage replacement. As used described herein, strengthening of a hydrogel may include one or more steps of drying, annealing, and rehydrating to influence the crystalline structure of the hydrogel. The methods may further involve securing a nanofibrous material to a surface of an implant, infiltrating a hydrogel into the nanofiber network, and annealing the hydrogel.

Approaches to creating synthetic cartilage by infiltrating a hydrogel into a nanofiber network for mimicking cartilage are described in International Patent Application No. PCT/US2021/040031, which is incorporated herein by reference in its entirety. The methods described herein may be used to form hydrogels that match or exceed the higher end of the range of strength of cartilage, while having a similar modulus, coefficient of friction, and resistance to wear of cartilage.

Described herein are hydrogels and methods of making and using them for mimicking or replacing cartilage, and that may be interdigitated with a nanofibrous network, such as a cellulose nanofiber network. The incorporated hydrogel may have a crystalline structure that imparts high tensile and/or compressive strength to the hydrogel. In some examples, a reinforced hydrogel for use in an implant described herein may include a cross-linked cellulose nanofiber network; and a hydrogel infused within interstitial regions of the cross-linked cellulose nanofiber network, wherein the hydrogel has a crystallinity of 20% or greater. In some examples, the hydrogel comprises polyvinyl alcohol (PVA). In any of these examples the hydrogel may exclude (or substantially exclude) PAMPS. The hydrogel may be >90% PVA (e.g., >92%, >93%, >94%, >95%, >96%, >97%, >98%>99%, etc.) of PVA that has been annealed as described herein.

As demonstrated herein, the crystallites formed during annealing strengthens an otherwise amorphous polymer hydrogel by acting as cross-links that redistribute applied stresses and hinder crack propagation. The crystallites also increase the solid content and strength of the hydrogel by reducing the amount of water taken up by the PVA after annealing.

Described herein are implants comprising: an implant body and a cellulose-reinforced hydrogel material comprising: a cross-linked cellulose nanofiber network bonded to the porous surface of the implant body by a cement; and a hydrogel impregnated in the cross-linked cellulose nanofiber network, wherein the hydrogel has a crystallinity of 20% or greater. The implant body may include a porous surface. For example, the implant body may be a titanium body with a bone-facing porous surface and a hydrogel-facing non-porous surface.

The hydrogels described herein may have a water content conducive to imparting high tensile and/or compressive strength to the hydrogel. In some examples, the hydrogel may have at least 20% by weight (wt %) of water and have a tensile strength exceeding that of cartilage, e.g., exceeding 40 Megapascals (MPa).

The composition of the interstitial hydrogel may be chosen to maximize crystallinity. For example, some hydrogel polymers and/or polymer mixtures have been found to hinder the crystalline formation, thereby decreasing the tensile and compressive strength of the composite hydrogel.

In general, the hydrogels may be comprised of one or more polymers that are conducive to forming crystalline structures. In some examples, the hydrogel may include polyvinyl alcohol (PVA). In some cases, the hydrogel may include only one type of polymer. In some variations, the hydrogel is comprises of one or more of: polyvinyl alcohol (PVA), poly(2-acrylamido-2-methyl-1-propanesulfonic acid sodium salt (PAMPS), poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, Guanine-boric acid reinforced PDMAAm, polyelectrolyte hydrogels, a poly(acrylonitrile-co-1-vinylimidazole) hydrogel (e.g., a mineralized poly (acrylonitrile-co-1-vinylimidazole) hydrogel), a polyacrylic acid-$Fe^{3+}$-chitosan hydrogel, a poly(methacrylic acid) gel, a Graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, a Agar-polyhydroxyethylmethacrylate gel, a polyfacryloyloethyltrimethylammonium chloride hydrogel, a poly(3-(methylacryloylamino)propyl-trimethyl-ammonium chloride hydrogel, a poly(sodium p-styrenbesulfonate) hydrogel, a polyethylene glycol diacrylate hydrogel, and a polyethylene glycol hydrogel. In some cases it may be beneficial to exclude PAMPS (e.g., having no PAMPS, having less than 0.1%, less than 0.5%, less than 1%, etc.).

The nanofiber network may comprise a cellulose nanofiber network. The nanofiber network may comprise a cross-linked cellulose nanofiber network. In some examples the nanofiber network comprises a bacterial cellulous (BC). Additionally or alternatively, the nanofiber network may comprise at least one of: electrospun polymer nanofibers, poly(vinyl alcohol) (PVA) nanofibers, aramid nanofibers, aramid-PVA nanofibers, wet-spun silk protein nanofiber, chemically crosslinked cellulose nanofiber, and polycaprolactone (PCL) fibers.

A cellulose-reinforced hydrogel may include: a cellulose nanofiber network; and a hydrogel impregnated in the cellulose nanofiber network, wherein the hydrogel has a crystallinity of 20% or greater. The cellulose-reinforced hydrogel material may have a tensile strength of 40 MPa or greater. The cellulose-reinforced hydrogel material may have a compressive strength of 59 MPa or greater.

Described herein is a cellulose-reinforced hydrogel comprising a water content of at least 20 wt % and a compressive strength exceeding 59 MPa. The cellulose-reinforced hydrogel may comprise bacterial cellulose and/or a hydrogel comprising polyvinyl alcohol (PVA).

Described herein is a method of forming a cellulose-reinforced hydrogel comprising: infiltrating a hydrogel in a cellulose nanofiber network to form the cellulose-reinforced hydrogel; and annealing the hydrogel to increase a crystalline content of the hydrogel. Annealing the hydrogel may include heating the cellulose-reinforced hydrogel. Annealing the hydrogel may include heating the cellulose-reinforced hydrogel to decrease a water content of the hydrogel. In some examples, the cellulose-reinforced hydrogel may be heated to a temperature ranging from 90-140° C. Annealing the hydrogel may include rehydrating the hydrogel. Rehydrating the hydrogel may include increasing a water content of the hydrogel to at least 20 wt %. The method may further include removing excess hydrogel from a surface of the cellulose nanofiber network. Removing excess hydrogel may include removing the excess hydrogel by hand or by molding the cellulose-reinforced hydrogel.

Described herein is an implant knee resurfacing comprising: a top bearing surface comprising a cellulose-reinforced hydrogel comprising: a cellulose nanofiber network; and a hydrogel impregnated in the cellulose nanofiber network, wherein the hydrogel has a crystallinity of 20% or greater.

The hydrogel (e.g., cellulose-reinforced hydrogel) may be attached to a metallic base with a shear strength exceeding 0.2 MPa.

When used for partial knee resurfacing, the implant may be configured to wear an opposing cartilage surface to an extent not significantly greater than the extent to which cartilage wears cartilage. A top bearing surface of the implant may have a coefficient of friction (COF) that is not statistically different from that of cartilage.

The implants described herein may be configured as a medical implant, and may include a tissue engaging portion (e.g., a bone engaging portion such as a rod, screen, nail, etc.). A first surface of the implant, to which a nanofiber network may be secured, may be porous. For example, the first surface may be greater than 40% porous to a depth of 1 mm or greater.

The nanofiber network may be secured to the implant (e.g., to a porous surface of the implant) by any appropriate method. For example, the nanofiber network may be secured to the implant by a cement, such as an α-TCP cement. In some examples the cement comprises one or more of: zinc oxide eugenol, glass ionomer, calcium silicate, polycarboxylate cement, zinc phosphate, resin-based (dental) cements, such as acrylate or methacrylate resin cements, which may contain silicate or other types of fillers in an organic resin matrix (for example, a methacrylate cement such as "RelyX™ Unicem 2 Self-Adhesive Resin Cement," or "RelyX™ Ultimate Adhesive Resin Cement"), and resin-modified glass ionomer cement. The cement may include an adhesive, such as (but not limited to) phosphoserine (PPS). In some variations the cement may include particles for reinforcement, such as stainless steel particles (e.g., stainless steel powder, SSP).

The cement may extend at least 5 microns into the nanofiber network from the first surface (e.g., 6 microns or more, 7 microns or more, 8 microns or more 10 microns or more, 15 microns or more, 20 microns or more, etc.). The cement may not be bonded to the hydrogel. In some examples, the cementing may be completed (and the cement set or dry) before impregnating with the hydrogel.

The cement may be bonded to the nanofiber network but not be bonded to the hydrogel directly. This may be a consequence of the method of forming the network-reinforced hydrogel, in which the nanofiber network (e.g., the cellulose nanofiber network) is first secured (e.g., cemented)

to the implant body, before impregnating the hydrogel. The cement may be cured onto the nanofiber network so that it does not directly bond to the hydrogel.

Other adhesives may include surgical adhesives such as cyanoacrylate, gelating/resorcinol/formaldehyde (GRF), and/or fibrin.

The implant may be formed of any appropriate biocompatible material. For example, the surface of the implant body may be titanium. The surface of the implant body may be one or more of: a stainless steel alloy, a titanium alloy, a Co—Cr alloy, tantalum, gold, niobium, bone, Al oxide, Zr oxide, hydroxyapatite, Tricalcium phosphate, calcium sodium phosphosilicate, poly(methyl methacrylate), polyether ether ketone, polyethylene, polyamide, polyurethane, or polytetrafluoroethylene.

As mentioned, the attachment surface in which a nanofiber network is secured may be porous. Alternatively, the attachment surface may be non-porous. For example, the attachment surface may be 20% or greater (30% or greater, 40% or greater, 50% or greater, 60% or greater, 70% or greater, etc.) porous, to a depth of 0.5 mm or greater (e.g., 0.6 mm, 0.7 mm, 0.8 mm, 0.9 mm, 1 mm or greater, etc.). As used herein, the percentage that the surface if porous (e.g., the percent porosity of the surface) may refer to the percentage of the surface within the depth that is absent, forming open spaces within the surface. These open spaces may refer to pores, some of which may be connected (e.g., in fluid connection) with each other. The attachment surface may generally be referred to herein as a top bearing surface because it may be configured to contact other surfaces (e.g., bone surfaces, etc.), and may be added to a load-bearing surface.

In any of these apparatuses (e.g., devices, systems, including implants), at least a portion of the nanofiber network may be mineralized. For example, at least a portion, such as the region near the interface with the surface, may be mineralized with hydroxyapatite. The mineralization may extend at least 5 microns into the nanofiber network (e.g., at least 7 microns, at least 8 microns, at least 9 microns, at least 10 microns, at least 15 microns, at least 20 microns, etc.) from the surface.

In general, the nanofiber network may be coupled to the top bearing surface of the implant. The cross-linked cellulose nanofiber network may be attached over the top load surface by clamping and/or by adhesive. For example, the nanofiber network may be bonded by cement to the top load surface; in some examples, the cement is not bonded to the hydrogel; the cement is only bonded to the nanofiber network. Alternatively, in some examples the nanofiber networks may be coupled to the implant, so that the nanofiber network, is secured over the top bearing surface without the use of a chemical adhesive, such as an epoxy. Instead, the nanofiber network may be secured over the top bearing surface by a clamp. For example, a clamp may secure the nanofiber network (e.g., one or more sheets of BC) over the top bearing surface around a periphery of the top bearing surface. Thus, in general, the use of an adhesive (such an epoxy) is optional.

Any appropriate implant may be used. The surface of the implant (e.g., top bearing surface, which may be equivalently referred to as simply the bearing surface) may be at least at the region to which the nanofiber network is attached over, may be titanium, stainless steel, etc. the bearing surface (e.g., top bearing surface) may be convex, flat, concave, or some mixture of these. For example, the surface of the implant body may comprise one or more of: a stainless steel alloy, a titanium alloy, a Co—Cr alloy, tantalum, gold, niobium, bone, Al oxide, Zr oxide, hydroxyapatite, Tricalcium phosphate, calcium sodium phosphosilicate, poly(methyl methacrylate), polyether ether ketone, polyethylene, polyamide, polyurethane, or polytetrafluoroethylene.

Also described herein are methods of making and/or using these implants. For example, described herein are methods of attaching a hydrogel to a surface so that the hydrogel is secured to the surface with a shear strength of greater than 1 MPa. Any of these methods may include: infiltrating a hydrogel in a cellulose nanofiber network to form the cellulose-reinforced hydrogel; and annealing the hydrogel to increase a crystalline content of the hydrogel. For example, annealing the hydrogel may include heating the cellulose-reinforced hydrogel. In some examples, annealing the hydrogel may include heating the cellulose-reinforced hydrogel to decrease a water content of the hydrogel. For example, the cellulose-reinforced hydrogel may be heated to a temperature ranging from 90-140° C. In some cases, annealing the hydrogel may include rehydrating the hydrogel. Rehydrating the hydrogel may include increasing a water content of the hydrogel to at least 20 wt %. The methods may also include removing excess hydrogel from a surface of the cellulose nanofiber network. Removing excess hydrogel may include removing the excess hydrogel by hand or by molding the cellulose-reinforced hydrogel.

In some examples, the outer surface of the hydrogel may be formed to be smooth (e.g., to have a roughness of less than 30 microns). For example, the methods described herein may include mechanically polishing an outer surface of the hydrogel to a roughness of less than 30 microns. In some cases, the outer surface may be formed smooth by molding, including molding the heated polymer using a smooth mold. For example, infiltrating the nanofiber network with hydrogel may include molding the hydrogel so that an outer surface of the hydrogel has a roughness of less than 30 microns. Molding the outer surface may also allow a manufacturer to form the outer surface into any desired shape. For example, the shape may be concave, convex, saddle shaped, etc. Any desired shape (and smoothness) may be formed, e.g., by molding and/or polishing.

In any of these methods securing the (e.g., dry) nanofiber network may include securing, such as clamping and/or cementing, a freeze-dried nanofiber network. As mentioned above, any of these devices and methods may use a dry nanofiber network that comprises a cellulose nanofiber network. The dry nanofiber network may comprise at least one of: electrospun polymer nanofibers, poly(vinyl alcohol) (PVA) nanofibers, aramid nanofibers, Aramid-PVA nanofibers, wet-spun silk protein nanofiber, chemically crosslinked cellulose nanofiber, or polycaprolactone (PCL) fibers.

Any of the methods described herein may include rehydrating the nanofiber network. Including rehydrating it after it has been secured to the implant surface.

Any of these methods may include mineralizing at least a portion of the nanofiber network adjacent to the surface.

Described herein are implants for knee resurfacing or partial knee resurfacing. For example, a top bearing surface of the implant may include a hydrogel having a water content of at least 20 wt %, in which the hydrogel is attached to a metallic base with a shear strength exceeding 0.2 MPa.

Any of the methods described herein may include mechanically polishing an outer surface of the hydrogel (e.g., cellulose-reinforced hydrogel) to a roughness of less than 50 microns (e.g., less than 50 microns, less than 40 microns, less than 30 microns, less than 25 microns, less than 20 microns, less than 15 microns, less than 10 microns, etc.). Mechanically polishing may include abrading the hydrogel that is attached to the surface as described herein with a fine grit sandpaper or equivalent.

Any of these methods may include rehydrating the nanofiber network. The nanofiber network may be rehydrated before impregnating with the hydrogel or the impregnation may rehydrate the nanofiber network.

For example, described herein are implants, comprising: an implant body having a top bearing surface; an anchoring base (which may extend from a back of the top bearing surface); and a cellulose-reinforced hydrogel comprising: a cross-linked cellulose nanofiber network secured over the top bearing surface of the implant body; and an interstitial hydrogel portion within interstitial regions of the cross-linked cellulose nanofiber network, wherein the interstitial hydrogel portion has a crystallinity of 20% or greater. The interstitial hydrogel portion may polyvinyl alcohol (PVA). The cellulose-reinforced hydrogel may comprise at least 20% by weight of water. The cellulose-reinforced hydrogel may have a tensile strength exceeding 40 MPa. The cross-linked cellulose nanofiber network may be chemically cross-linked. The cross-linked cellulose nanofiber network may comprise bacterial cellulose (BC). The cellulose-reinforced hydrogel may have a compressive strength exceeding 59 MPa. The cross-linked cellulose nanofiber network may be secured over the top bearing surface by a clamp. In some examples the cross-linked cellulose nanofiber network comprises one or more sheets of bacterial cellulous (BC) held over the top bearing surface by a clamp secured to a lip or rim of the top bearing surface. The clamp may be used to secure the cross-linked cellulose nanofiber network without the need for epoxy. Alternatively any of these implants may include an adhesive.

Also described herein are methods of forming an implant having a cellulose-reinforced hydrogel, comprising: attaching a cross-linked cellulose nanofiber network to a top bearing surface of the implant; infiltrating a hydrogel component within interstitial regions of the cross-linked cellulose nanofiber network to form the cellulose-reinforced hydrogel; and annealing the cellulose-reinforced hydrogel so that a crystalline content of the hydrogel component has a crystallinity of 20% or greater. The hydrogel component may comprise polyvinyl alcohol (PVA). Annealing the cellulose-reinforced hydrogel may include heating the cellulose-reinforced hydrogel. For example, annealing the cellulose-reinforced hydrogel may comprise heating the cellulose-reinforced hydrogel to decrease a water content of the cellulose-reinforced hydrogel. In some examples the cellulose-reinforced hydrogel is heated to a temperature ranging from 90-140° C. Annealing the cellulose-reinforced hydrogel may comprise rehydrating the cellulose-reinforced hydrogel. Rehydrating the cellulose-reinforced hydrogel may comprise increasing a water content of the cellulose-reinforced hydrogel to at least 20 wt %. Any of these methods may include removing excess of the hydrogel component from a surface of the cross-linked cellulose nanofiber network. For example, excess of the hydrogel component may be removed by hand or by molding the cellulose-reinforced hydrogel. In any of these examples the cross-linked cellulose nanofiber network may comprise bacterial cellulose (BC). In some examples attaching the cross-linked cellulose nanofiber network to the top bearing surface comprises clamping the cross-linked cellulose nanofiber around a periphery of the top bearing surface.

Also described herein are implants for a knee resurfacing, the implant comprising: a top bearing surface comprising a cellulose-reinforced hydrogel comprising: a cellulose nanofiber network; and a hydrogel component impregnated in the cellulose nanofiber network, wherein the hydrogel component has a crystallinity of 20% or greater. The hydrogel component may comprise polyvinyl alcohol (PVA). The cellulose-reinforced hydrogel may comprise at least 20% by weight of water. The cellulose-reinforced hydrogel may have a tensile strength exceeding 40 MPa. The cellulose-reinforced hydrogel may be attached to a metallic base of the top bearing surface with a shear strength exceeding 0.2 MPa. The top bearing surface may have a coefficient of friction (COF) that is not statistically greater than that of cartilage.

In general, the methods and apparatuses described herein may be used with any of the methods, apparatuses and compositions described in International Patent Application No. PCT/US2021/040031, titled "NANOFIBER REINFORCEMENT OF ATTACHED HYDROGELS," filed on Jul. 1, 2021, which is herein incorporated by reference in its entirety.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings.

FIGS. 3A-3E are graphs illustrating effects of annealing on the mechanical properties of various hydrogel compositions: FIG. 3A illustrates a tensile stress-strain curve for PVA hydrogels annealed at different temperatures; FIG. 3B illustrates a compressive stress-strain curve for PVA hydrogels annealed at different temperatures; FIG. 3C illustrates tensile strength and moduli of PVA annealed at different temperatures; FIG. 3D illustrates compressive stress at 0.8 strain and moduli of PVA annealed at different temperatures; and FIG. 3E illustrates crystallinity and solid content weight fraction of PVA annealed at different temperatures.

FIGS. 4A-4E are graphs illustrating effects of annealing on the mechanical properties of BC-PVA hydrogel. FIG. 4A illustrates a tensile stress-strain curve for BC-PVA hydrogels annealed at different temperatures; FIG. 4B illustrates a compressive stress-strain curve for BC-PVA hydrogels annealed at different temperatures; FIG. 4C illustrates tensile strength and moduli of BC-PVA annealed at different temperatures; FIG. 4D illustrates compressive stress at 0.8 strain and moduli of BC-PVA annealed at different temperatures; and FIG. 4E illustrates crystallinity and solid content weight fraction of BC-PVA annealed at different temperatures.

FIG. 5A illustrates tensile strength, tensile moduli and solid content weight fraction of BC-PVA-PAMPS hydrogels that were made with solutions containing different concentrations of the AMPS monomer, where BC-PVA samples were annealed before infiltration of AMPS; and FIG. 5B illustrates compressive strength and moduli of BC-PVA-PAMPS hydrogels.

FIG. 6A illustrates a schematic for how the wear and COF of hydrogels versus cartilage was measured; FIG. 6B illustrates Micro-CT cross-section images of the cartilage and hydrogel samples; FIG. 6C illustrates the wear depth of cartilage and hydrogel samples after 106 cycles under 1 MPa of pressure, a spin rate of 100 mm/s, and with FBS as the lubricant; and FIG. 6D illustrates the COF between cartilage and the hydrogels during the tests over 24 hours.

FIG. 7A illustrates a schematic for how the wear of cartilage versus hydrogels was measured; FIG. 7B illustrate Micro-CT cross-section images; and FIG. 7C illustrates the wear depth of cartilage and hydrogel samples after 106 cycles under 1 MPa of pressure, a spin rate of 100 mm/s, and with FBS as the lubricant.

FIG. 8A illustrates results for shear testing of pig cartilage and hydrogels secured to metal pins with adhesive and shape memory alloy clamps; FIG. 8B illustrates an image of an osteochondral plug extracted from a pig knee after testing to failure; FIG. 8C illustrates an image of a BC-PVA-PAMPS hydrogel (fabricated with a freeze-thaw process) after testing to failure; and FIG. 8D illustrates an image of a BC-PVA hydrogel (fabricated by annealing at 90° C. and rehydrated) after testing to failure.

FIGS. 9A-9F show front and side views of an annealed BC-PVA hydrogel incorporated in an implant for partial knee resurfacing before and after undergoing mechanical stress.

FIG. 12A is an image illustrating one example of a method of attaching a hydrogel to a metallic plug, including using a clamp (e.g., a shape memory alloy clamp).

FIGS. 12B and 12C illustrate examples of a fixture that may be used for aligning forming the materials described herein (e.g., aligning the BC, including a rod, cut BC, and ring clamp) as described herein: FIG. 12B shows a perspective view of the fixture; and FIG. 12C shows a sectional view through the fixture.

FIG. 12D is an image showing an exemplary sheet of bacterial cellulose (BC) cut (e.g., with legs or crenellations) for wrapping over the edge of a bearing surface (e.g., metal rod, head, etc.).

FIG. 12E is diagram denoting the diameter D, length L, and width W dimensions of one example of a sheet.

FIG. 13 is an example of one test fixture that may be used to test searing of cartilage off of bone and/or a hydrogel material off of a test rod.

FIG. 14A shows an example of a process for attaching the BC-PVA-PAMPS hydrogel to a titanium implant for treatment of osteochondral defects. FIGS. 14B and 14C show repair of an implant.

FIG. 16A shows an increase in hydrogen bonding that occurs upon annealing.

DETAILED DESCRIPTION

Described herein are hydrogel compositions for the long-term repair of cartilage. The hydrogels have a crystalline structure that impart tensile and compressive strengths to the hydrogels that equal or exceed that of cartilage. The hydrogels may be incorporated in a nanofiber network (e.g., cellulose) to increase wear properties and/or to facilitate attachment to an implant body. The hydrogels are found to withstand the high compressive and shear stresses associated movement of the knee joint, and are thus well-suited for implementation on knee implants. The hydrogels may be characterized by one or more attributes and properties, such as crystalline structure, tensile strength, compressive strength, water content, coefficient of friction (COF), and/or other attributes and properties.

The methods of forming hydrogel implants described herein can be used to create hydrogel-coated orthopedic implants with surfaces that mimic or improve on the mechanical and/or tribological properties of cartilage. Previously methods of forming implants with hydrogels comprising a bacterial cellulose (BC) network infused with polyvinyl alcohol (PVA) and poly(2-acrylamido-2-methyl-1-propanesulfonic acid sodium salt (PAMPS), referred to as BC-PVA-PAMPS hydrogels, are described in International Patent Application No. PCT/US2021/040031, which is incorporated herein by reference in its entirety. In preparing the BC-PVA-PAMPS hydrogel, a freeze-thaw method is used to gel a PVA-water mixture after infiltration into the BC. This freeze-thaw gelation step was used to increase the strength of the PVA hydrogel, and to prevent dissolution of the PVA in a following PAMPS infiltration step. The increase in strength upon freezing and thawing the PVA is attributed to crystallization of the PVA chains and phase segregation.

Methods described herein improve upon these previous methods by enhancing the mechanical properties of the reinforced hydrogels, thereby improving performance of the implant, even when subjected to high impact and shear forces. For example, the tensile and compressive strength of the reinforced hydrogel may be increased up to and beyond that of cartilage. The methods involve a mechanical strengthening process that increases the crystallinity and decreases the water content of PVA relative to the freeze-thaw process. The mechanical strengthening process may include drying, annealing, and/or rehydrating of the hydrogel. When implemented on a hydrogel, the crystalline structure within the hydrogel may be increased despite being interdigitated within the fibrous network. In addition, the hydrogel may be substantially bubble-free and crack-free after undergoing the crystal restructuring process.

Figure 1A:
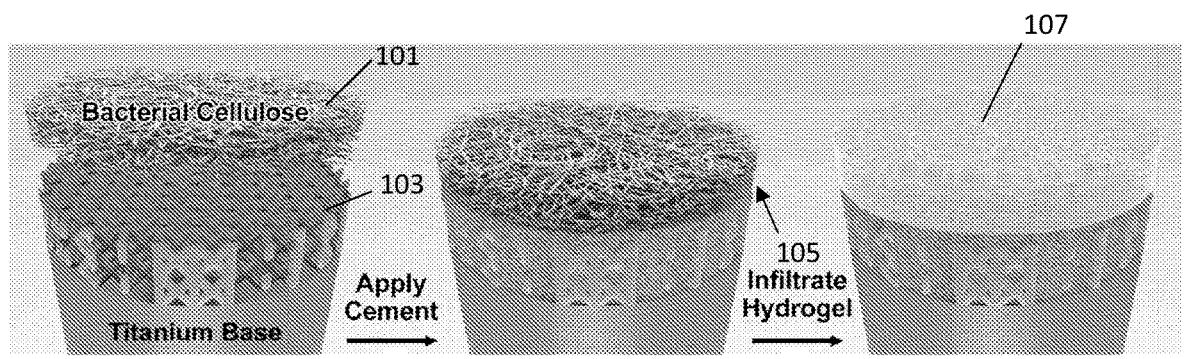
FIG. 1A is an illustration of an exemplary process for attachment of a hydrogel to a porous base by a Nanofiber-Enhanced STicking (NEST) method. In this example, a nanofibrous sheet (e.g., bacterial cellulose) is attached to a surface (e.g., a porous base such as porous titanium) with an adhesive (e.g. α-TCP cement), after which the hydrogel components are infiltrated into the nanofibrous sheet.
Figure 1B:
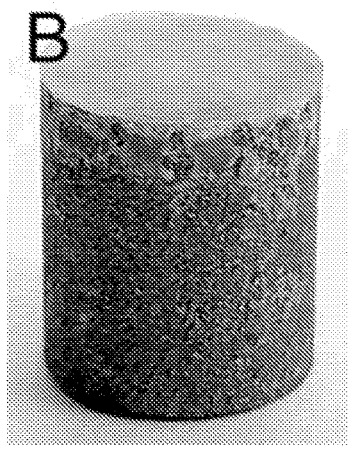
FIG. 1B shows an example of a hydrogel bonded to a titanium plug.
Figure 1C:
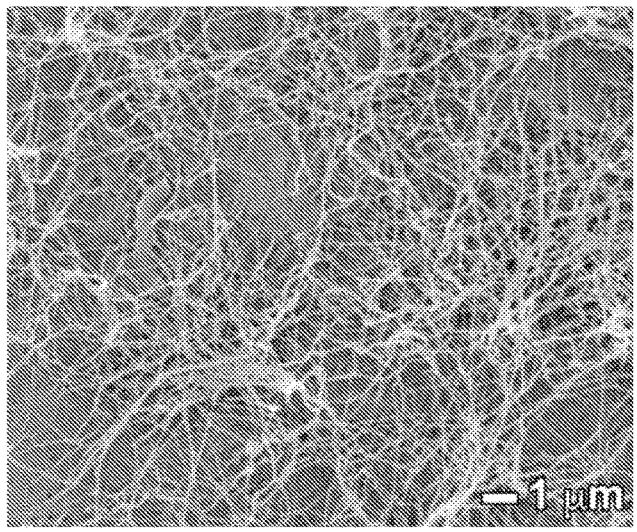
FIG. 1C shows an SEM image of a surface of an exemplary freeze-dried bacterial cellulose sheet.

FIGS. 1A-1C illustrate an example of an apparatus in which a hydrogel has been bonded to an implant surface as described herein. The hydrogel may be coupled to the implant surface by first attaching a layer of nanofibrous material, such as cellulous (e.g., bacterial cellulous) to an implant base using an adhesive (e.g., cement). The nanofibrous material may be dry (e.g., before attaching to the implant base). The attaching surface of the implant base may be porous, for example, to enhance adhesion. The nanofibrous layer may then be infiltrated with a hydrogel component. In this way, the nanofibrous portion may be secured with an adhesive (e.g., cement) that can penetrate and secure the porous bacterial cellulose network to the surface and may create an interdigitating bond without the interference of water. Once the hydrogel component is infiltrated within the nanofibrous network, the reinforced hydrogel may be processed (e.g., annealed) to change the crystalline structure of the hydrogel component, thereby enhancing mechanical properties of the reinforced hydrogel.

For example, in FIG. 1A, the nanofibrous portion is bacterial cellulose (BC) 101 that is applied to the prepared surface of the implant (shown in this example as a titanium base, having pores) 103. A cement (e.g., any appropriate medical or dental grade cement may be used) is applied, and secures the dry bacterial cellulose to the implant surface. Thereafter the hydrogel component may be infiltrated into the nanofibrous portion, resulting in the complete hydrogel 107 attached to the base 103 via the bacterial cellulose 101. The reinforced hydrogel 107 then undergoes a crystal restructuring process to enhance its mechanical properties.

FIG. 1B shows an example of a titanium implant (e.g., plug) to which a cellulous-reinforced hydrogel has been attached, as described herein. In this example, the nanofibrous portion (e.g., BC) of the hydrogel is bonded via an adhesive to the porous surface of the implant, and the hydrogel is linked to the nanofibrous portion. Any appropriate adhesive (e.g., cement) may be used to adhere the nanofibrous portion of the hydrogel to the surface of the implant. In some variation the cement is $\alpha$-tricalcium phosphate ($\alpha$-TCP), a hydroxyapatite-forming cement that may be used for attachment of the hydrogel due to its biocompatibility, osteoconductivity, and shear strength, which may exceed that of cyanoacrylate. In some cases, $\alpha$-TCP is combined with phosphoserine (PPS) to promote adhesion. In some cases, the hydroxyapatite is reinforced with stainless-steel powder (SSP) (e.g., with an average particle size of 150 $\mu$m) to hinder crack propagation. As will be described in greater detail below, in some examples an adhesive is not used, and the nanofiberous portion is secured to the bearing surface by a mechanical means (such as a clamp).

As described herein, the nanofibrous portion (e.g., BC) may be treated to dried (e.g., freeze-dried) to increase adhesion to the nanofibers. FIG. 1C is a scanning electron microscope (SEM) image of the surface of an exemplary freeze-dried piece of BC, which shows that it consists of many nanoscale fibers that present a large surface area for attachment with an adhesive. In some examples, multiple freeze-thaw cycles are performed, which may increase tensile strength (once the hydrogel is infused therein) and/or increase the shear strength of the adhesion of the reinforced hydrogel to the implant base.

As mentioned above, a previous approach to creating a cartilage-equivalent hydrogel involves infiltrating a bacterial cellulose (BC) nanofiber network with polyvinyl alcohol (PVA) and poly(2-acrylamido-2-methyl-1-propanesulfonic acid sodium salt) (PAMPS). This hydrogel exhibited a tensile strength of 22.6 MPa and a compression strength of 20 MPa. In comparison, the range of tensile and compression strengths reported for human cartilage are 8.1-40 MPa and 14-59 MPa, respectively. Thus, there is room to improve the strength of hydrogels to be at the higher end of the range of strengths reported for cartilage, or to exceed cartilage in strength, while having a similar modulus, coefficient of friction, and resistance to wear as cartilage. Given the higher tensile strength of annealed PVA relative to freeze-thawed PVA, tests were performed to determine whether changing from a freeze-thaw to annealing process can improve the mechanical strength of a BC-PVA-PAMPS hydrogel while retaining adequate control over the hydrogel shape and defect content. Given the tensile strength of a BC-PVA-PAMPS hydrogel (22.6 MPa), is already similar to the tensile strength of a PVA hydrogel made by annealing (20 MPa), it was not obvious that switching to the annealing process for a BC-reinforced hydrogel would yield further improvements in the mechanical strength. In addition, the presence of BC or PAMPS could potentially interfere with the crystallization of PVA that occurs during the annealing process, thereby hindering the improvement in mechanical strength that occurs as a result of crystallization. It was also not clear whether it would be possible to obtain high-quality, bubble-free, crack-free samples after annealing PVA reinforced with BC. Obtaining samples that are as free of defects as possible may be necessary to maximizing the mechanical strength of the hydrogel. Finally, it was unclear whether the lower water content of the annealed hydrogel might cause the COF and opposing surface wear to be too high.

As demonstrated herein, reinforcement of annealed PVA with BC leads to a 3.2-fold improvement in the tensile strength (from 15.6 to 50.5 MPa) and a 1.7-fold increase in the compressive strength (from 56.7 to 95.4 MPa). The highly crystallized BC-PVA hydrogel that results from annealing is the first hydrogel with a tensile and compressive strength that exceeds that of cartilage. Reinforcement of the PVA with BC may essentially eliminate the deformation and bubbles that would otherwise occur during annealing. When tested against cartilage, annealed BC-PVA wore an opposing cartilage surface to the same extent as cartilage and was three times more resistant to wear than cartilage. The COF of BC-PVA against cartilage was equivalent to that of cartilage against cartilage. In contrast to results with freeze-thawed BC-PVA, addition of PAMPS to the annealed BC-PVA decreased the tensile strength of the hydrogel due to a loss of crystallized PVA and an increase in water content. The improved tensile strength of annealed BC-PVA enabled it to attach to a metal base with a shear strength 68% greater than the shear strength of cartilage on bone. The high strength, high wear resistance, and low COF of annealed BC-PVA make it an excellent material for replacing damaged cartilage.

The tests and measurements performed and described herein on various hydrogel compositions demonstrate how certain hydrogel compositions that undergo one or more strengthening processes, such as an annealing process, may increase the strength of a hydrogel to the upper limits or exceeding that of cartilage while attaining other characteristics (e.g., coefficient of friction) similar to that of cartilage.

Figure 2A:
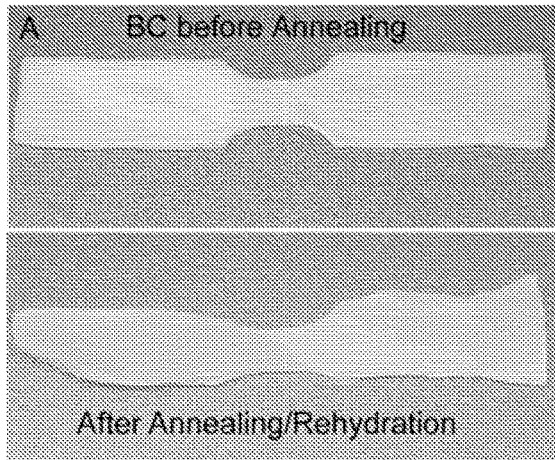
FIGS. 2A-2D show various hydrogel samples before and after annealing and rehydration to illustrate the effects on the morphology of different hydrogel compositions.
Figure 2B:
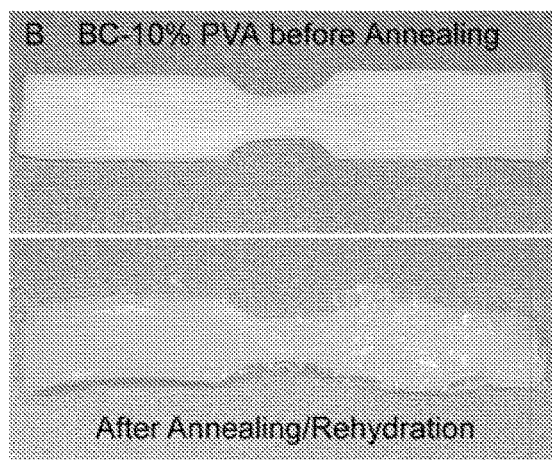
Figure 2C:
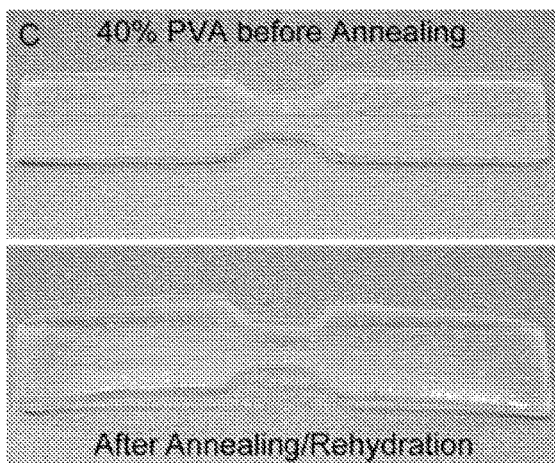
Figure 2D:
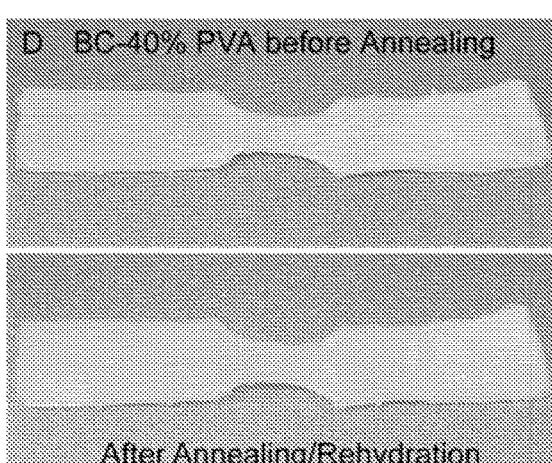

One potential disadvantage of annealing a hydrogel is that the hydrogel may develop bubbles and cracks, especially as the sample thickness increases or water content increases. FIGS. 2A-2D show various hydrogel samples before and after annealing and rehydration to illustrate the effects on the morphology of different hydrogel compositions. In particular, these samples illustrate the effect of the hydrogel composition on the shape of the sample after drying, annealing and rehydration. All samples were annealed at 90° C. for 25 hours and rehydrated in phosphate-buffered saline (PBS) solution for 24 hours at 23° C. FIG. 2A shows a sample of BC (without PVA), demonstrating how the BC sample became wrinkled and folded at the edges after annealing and rehydration. FIG. 2B shows a sample of BC that was annealed in a solution of 10 wt % PVA. As shown, the BC annealed in 10 wt % PVA solution also demonstrating substantial deformation. A PVA layer formed on top of the BC after annealing contains a large number of bubbles and easily delaminates from the BC film. The bubbles may be the result of the evaporation of water. FIG. 2D shows a sample 40 wt % PVA before and after annealing, demonstrating that such hydrogel also formed a large number of bubbles and deformed during the annealing process.

FIG. 2E shows a BC sample that was infiltrated with 40 wt % PVA in a hydrothermal bomb for 24 hours at 120° C. before annealing and rehydration. As shown, reinforcement of 40 wt % PVA with BC allowed the hydrogel to retain its shape with little to no deformation after annealing. This lack of deformation may be attributed to the higher solid content and tensile modulus of the BC-reinforced PVA. That is, the nano scale network of the BC layer appears to suppress the formation of the large bubbles that are visible in the 40 wt % PVA sample (FIG. 2C). A comparison of FIG. 2B to FIG. 2D indicates that the approach of infiltrating a high concentration of PVA into BC in a hydrothermal bomb, followed by removal of excess PVA from the BC surface, results in a more uniform hydrogel than if a BC sample is placed in a more dilute PVA solution that is concentrated via drying. These results demonstrate that, unlike BC alone, PVA alone, or the combination of BC with a 10 wt % of PVA, the BC infiltrated with 40 wt % PVA could retain its shape and remain relatively free of bubbles and other defects after annealing.

Figure 3A:
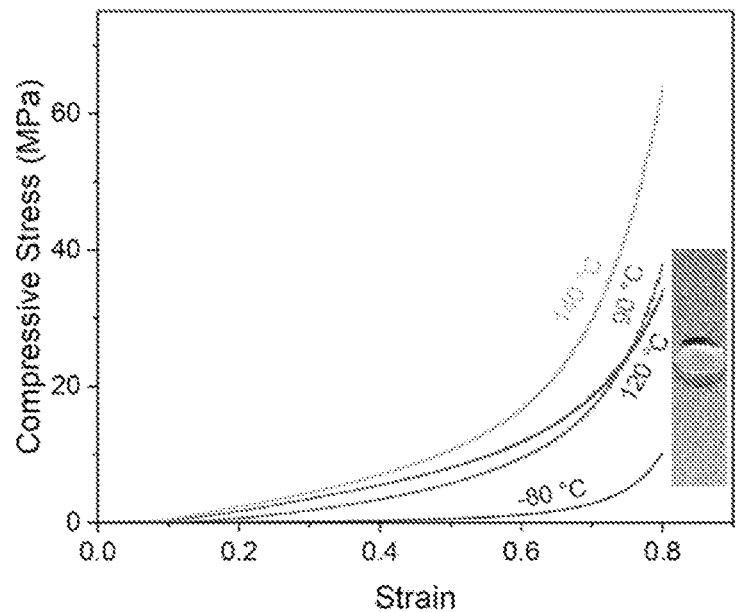
Figure 3B:
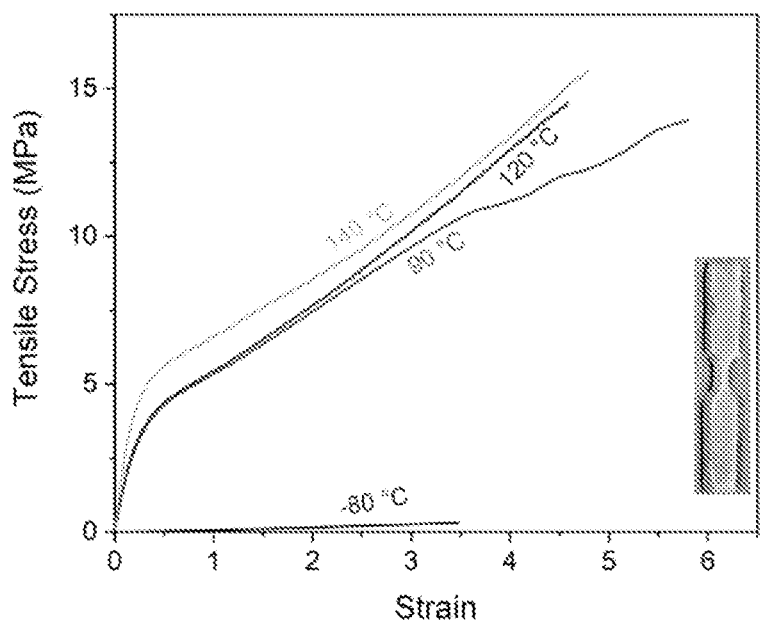

FIGS. 3A-3E illustrate the effects of annealing on the mechanical properties of various hydrogel compositions, where the effects of annealing on a PVA hydrogel were analyzed as a reference point. The PVA was fully hydrolyzed with a molecular weight of 145,000 g mol-1. A 40 wt. % PVA solution was dried at 90° C. for 24 hours, annealed at 90° C., 120° C. or 140° C., and then placed in a 0.15 M PBS solution for 24 hours for rehydration. PVA samples that underwent a freeze-thaw cycle were tested for comparison. FIGS. 3A and 3B show that annealing the hydrogel dramatically increased the tensile and compressive strength relative to samples that had undergone a freeze-thaw cycle. FIGS. 3C and 3D show that, relative to the freeze-thaw process, annealing increased the tensile strength by 60 times (from 0.26 to 15.6 MPa) and the compressive strength by 9 times (from 14.8 to 140.8 MPa). Increasing the annealing temperature from 90° C. to 140° C. led to an increase in the tensile strength and modulus. The increase in strength and modulus has been ascribed to the increase in the crystallinity and solid content of the hydrogel after annealing. FIG. 2E confirms that the crystallinity and solid content of the annealed PVA hydrogels are much greater than that of a freeze-thawed PVA hydrogel. For example, a PVA hydrogel made via the freeze-thaw process has an overall solid content of 0.09 and a PVA crystallinity of 0.21, whereas a PVA hydrogel made via annealing at 90° C. has an overall solid content of 0.42 and a PVA crystallinity of 0.58. The crystallites formed during annealing strengthens the otherwise amorphous PVA by acting as tough cross-links that redistribute applied stresses and hinder crack propagation. The crystallites also increase the solid content and strength of the hydrogel by reducing the amount of water taken up by the PVA when it is soaked in 0.15 M PBS after annealing.

Figure 4A:
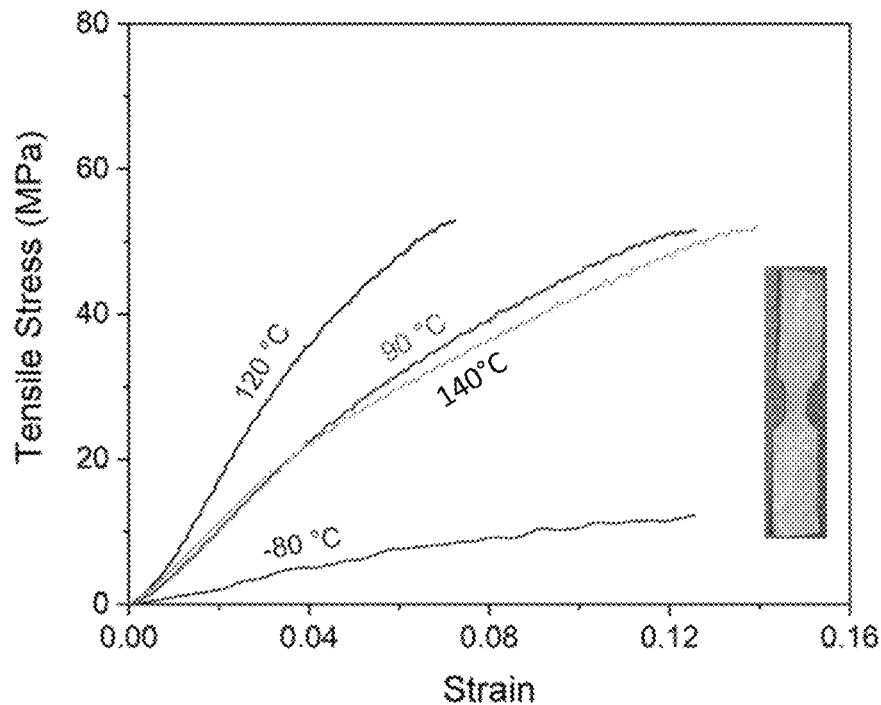
Figure 4B:
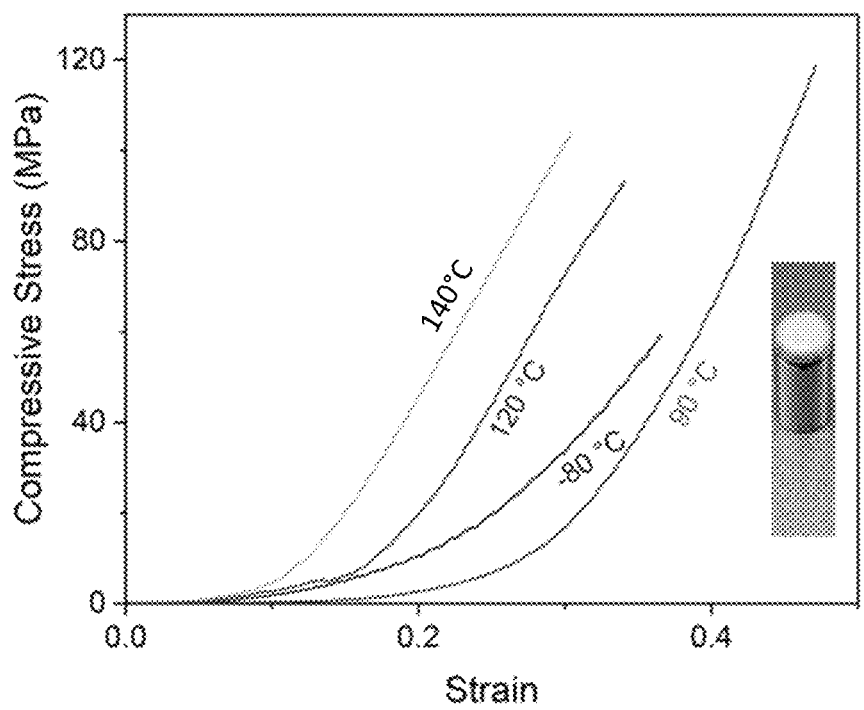

FIGS. 4A-4E illustrate the effect of annealing on a BC-PVA hydrogel. The same annealing process to PVA hydrogel described above with reference to FIGS. 3A-3E was applied to BC-PVA hydrogels. As with the PVA hydrogels, the BC-PVA hydrogels were dried at 90° C. for 24 hours, annealed at 90° C., 120° C. or 140° C., and then placed in a 0.15 M PBS solution for 24 hours for rehydration. FIGS. 4A and 4C show the tensile strength of the annealed BC-PVA hydrogels reached 50.4 MPa, an increase of 4.6 times relative to the BC-PVA that went through a freeze-thaw cycle, and an increase of 3.2 times relative to annealed PVA that was not reinforced with BC. FIGS. 4B and 4D show the compressive strength increased from 55.32 MPa to 95.35 MPa after annealing. Similar to the PVA hydrogel, this dramatic increase in strength can be attributed to the increase in crystallinity and solid content after annealing. FIG. 3E shows the crystallinity of the BC-PVA hydrogel increased from 0.07 after a freeze-thaw cycle to 0.4 after annealing. The solid weight fraction of the BC-PVA hydrogel increased from 0.11 after a freeze-thaw cycle to 0.53 after annealing. These results shows that PVA can still form crystallites within the nanofibrous BC network, and that these crystallites increase the solid content and strength of the hydrogel.

Figure 5A:
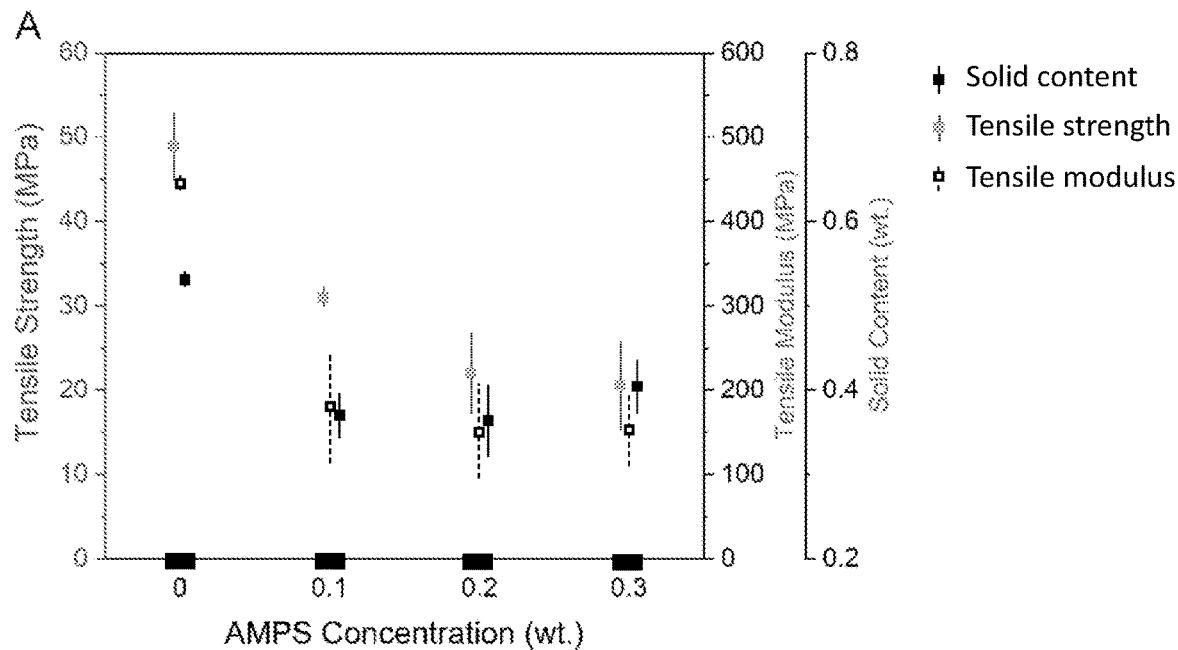
FIGS. 5A and 5B are graphs illustrating effects of PAMPS on an annealed BC-PVA hydrogel.
Figure 5B:
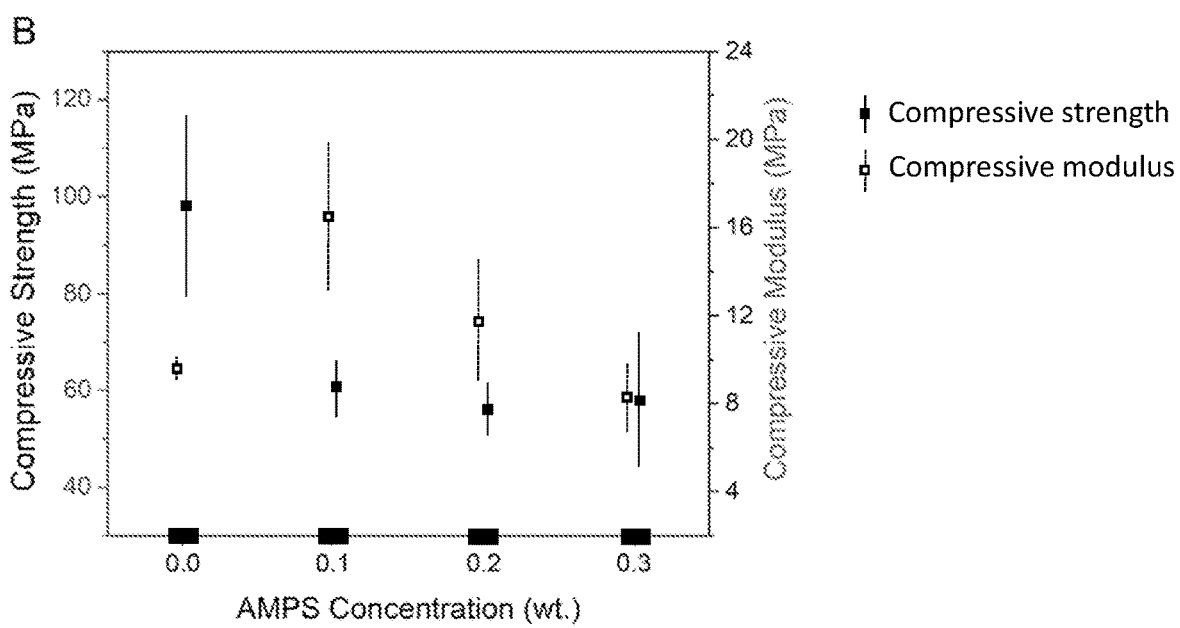

FIGS. 5A and 5B illustrate the effect of PAMPS on an annealed BC-PVA hydrogel. As mentioned above, it was previously found that the incorporation of PAMPS into a BC-PVA hydrogel made with a freeze-thaw cycle resulted in an increase in the tensile and compressive strength of the hydrogel. Thus, PAMPS was incorporated into an annealed BC-PVA hydrogel to determine the effect of the addition of PAMPS. As shown in FIG. 5A, the addition of PAMPS into the annealed BC-PVA hydrogel led to a decrease in the solid content relative to BC-PVA alone, from 0.53 to 0.37. Differential scanning calorimetry (DSC) thermograms show that after the addition of 10 wt % PAMPS, the peak from melting crystalline PVA disappeared, indicating the addition of PAMPS destroys the PVA crystallites that form during the annealing process. The decrease in solid content and loss of crystallinity upon addition of PAMPS led to a decrease in the tensile strength (from 48.9 MPa to 20.8 MPa), tensile modulus (from 444.8 MPa to 150.5 MPa) and compressive strength (from 98.1 MPa to 56.0 MPa in FIG. 5B) of the hydrogel. The increase in water content of the hydrogel and loss of strength was likely due to the fact that PAMPS is a negatively charged polymer, and this negative charge results in an osmotic pressure that swells the hydrogel with water.

Figure 6A:
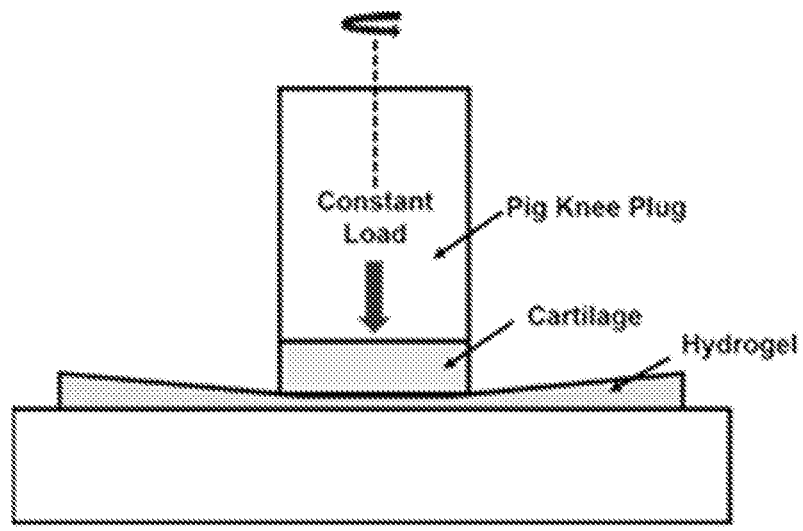
FIGS. 6A-6D illustrate various aspects of measuring wear and coefficient of friction (COF) of various hydrogel compositions and comparing such measurements against cartilage.
Figure 6B:
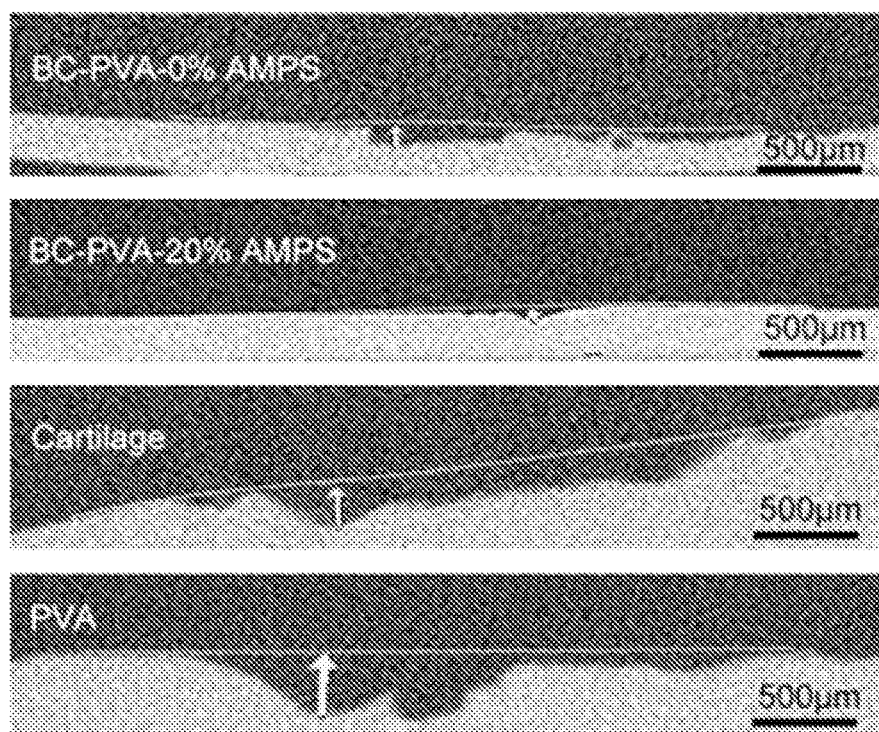
Figure 6C:
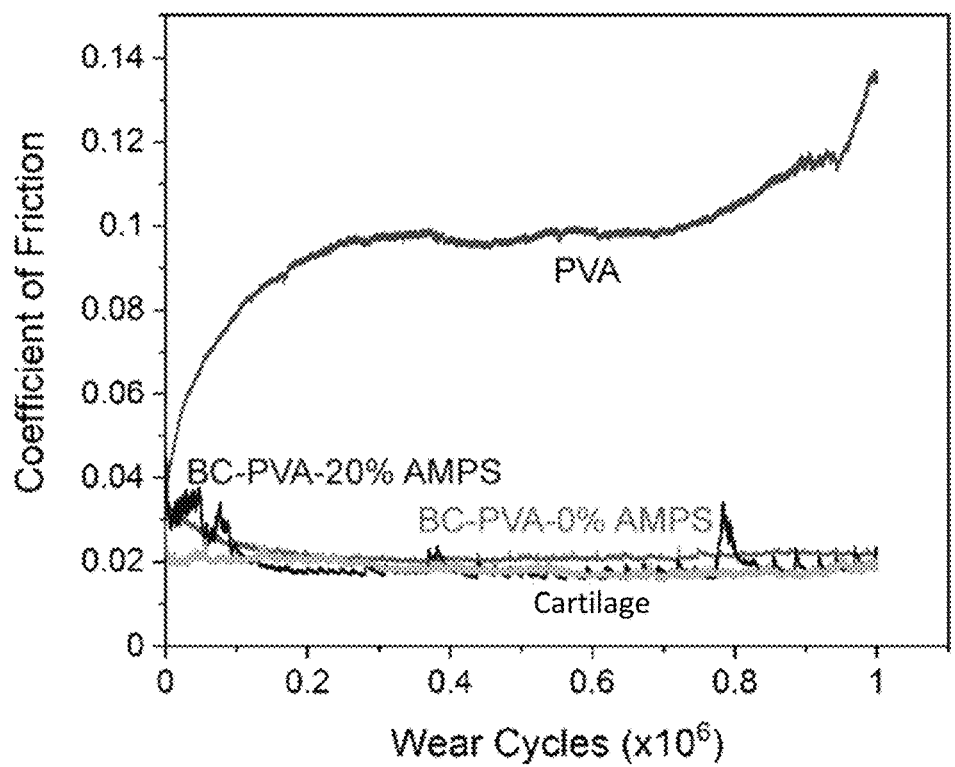
Figure 6D:
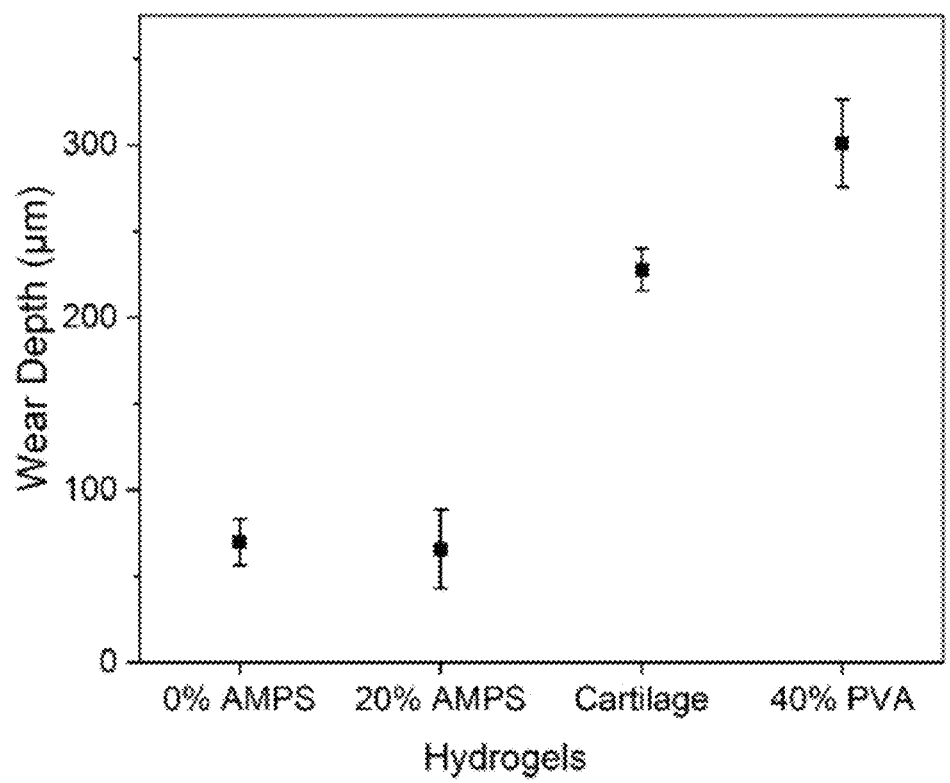

FIGS. 6A-6D illustrate various aspects of measuring wear and coefficient of friction (COF) of various hydrogel compositions and comparing such measurements against cartilage. FIG. 6A is a schematic illustration of an example of how a wear test is performed. A pin-on-disc configuration described in Example 11 below for testing the wear of hydrogels in fetal bovine serum (FBS) was used. A porcine cartilage plug was rotated against the hydrogel surface 106 times under 1 MPa of pressure and at a speed of 319 rotations per minute (maximum linear velocity was 100 mm $s^{-1}$). The wear resistance of a potential replacement for cartilage exceeds that of cartilage to ensure durability and minimize the generation of wear debris that could potentially cause an adverse biological reaction. The wear resistance of a BC-PVA-PAMPS hydrogel was previously shown to be equivalent to that of cartilage and to be superior to PVA or PVA-PAMPS when tested against a stainless-steel pin. These hydrogels were made by applying a freeze-thaw cycle to crystallize the PVA. FIGS. 6B-6D compare the wear resistance of PVA-based hydrogels (PVA, BC-PVA, and BC-PVA-PAMPS) that have been dried and annealed at 90° C. to that of porcine cartilage when tested against a porcine cartilage plug in FBS.

FIG. 6B shows cross-sectional Micro-CT images of the hydrogels that were acquired in the center of the wear mark to measure the maximum wear depth. FIG. 6C compares the wear depth of the hydrogels and cartilage. The wear depth of the BC-PVA hydrogel with 0% AMPS was 70.1 µm. The addition of 20% AMPS decreased the mean wear depth to 65.9 µm, but the difference between the 0% and 20% AMPS samples was not statistically significant. This comparison illustrates that the negative charge and higher water content caused by incorporating PAMPS into an annealed BC-PVA hydrogel does not significantly improve the wear resistance. Both of these values were 3 times lower than the wear depth on the cartilage sample, which was 227.8 µm. The wear depth for annealed and rehydrated PVA was 301.0 µm, four times greater than either BC-PVA sample. These results indicate the presence of BC in the hydrogel can dramatical improve the wear resistance of an annealed PVA hydrogel to be superior to that of cartilage.

The COF was recorded during the wear test, as shown in FIG. 6D. Cartilage maintained a constant COF of 0.020 during the test. The COF of BC-PVA decreased during the test from 0.040 to 0.021. The BC-PVA hydrogel with 20% AMPS had a similar COF as that without AMPS. In contrast, the COF of PVA increased dramatically during the test, from 0.033 to 0.135. Previous work has similarly demonstrated the COF of PVA against cartilage increases over time while the COF of cartilage against cartilage is constant. The increase in the COF for a PVA-Cartilage interface has been ascribed to transfer of damaged PVA to the cartilage surface, which, in turn, decreases the ability of the cartilage surface to maintain a lubricating water layer. The incorporation of BC into PVA clearly inhibits damage of the hydrogel, allowing it to maintain a low coefficient of friction similar to that cartilage during the wear test. The presence of AMPS in the hydrogel does not appear to be necessary for maintaining a low COF and high resistance to wear.

Figure 7A:
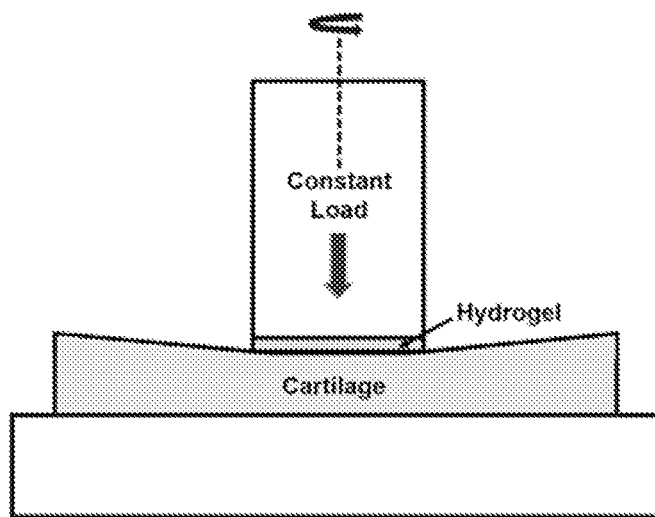
FIGS. 7A-7C illustrate various aspects of measuring wear of various hydrogel compositions and comparing such measurements against cartilage.

The materials used for cartilage replacement on one side of the joint, i.e., on the femoral condyle, should not cause wear of cartilage on the opposing surface, i.e., the tibial plateau. Traditional orthopedic materials like cobalt-chrome and ultra-high molecular-weight polyethylene are known to damage an opposing cartilage surface to a greater extent than hydrogels due to the higher COF and hardness of traditional orthopedic materials. To assess the wear caused by BC-PVA and BC-PVA-PAMPS hydrogels on cartilage, hydrogel plugs were created for wear testing (see Example 7 below). The hydrogel plugs were pressed against cartilage samples (see FIG. 7A) with 1 MPa of pressure, and rotated 106 times at a speed of 319 rotations per minute (the maximum linear velocity at the circumference of the pin was 100 mm s$^{-1}$).

Figure 7B:
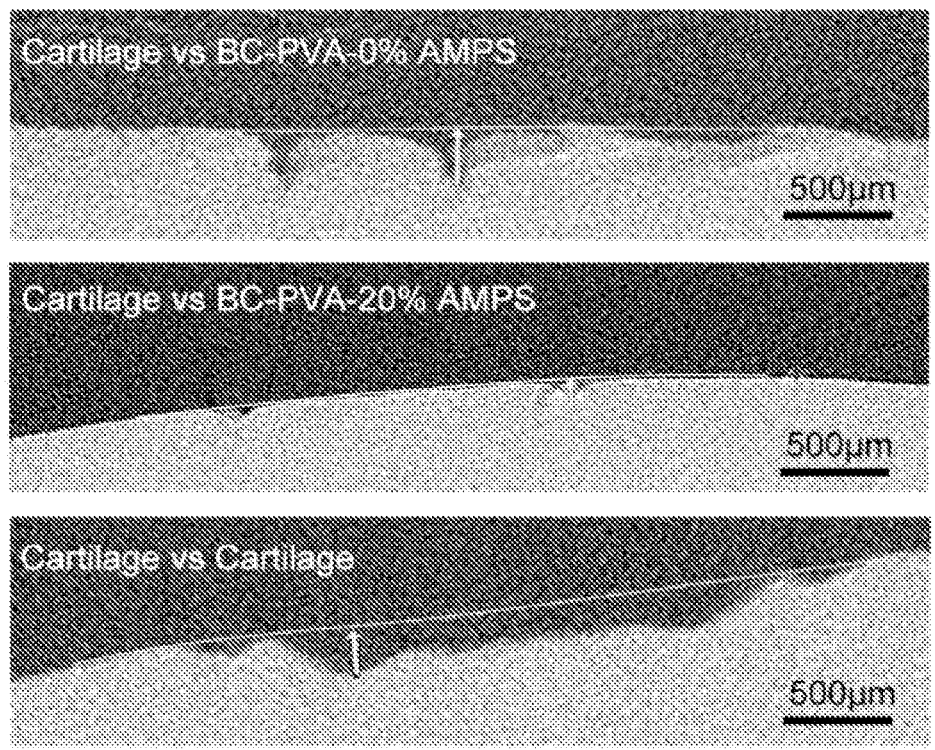
Figure 7C:
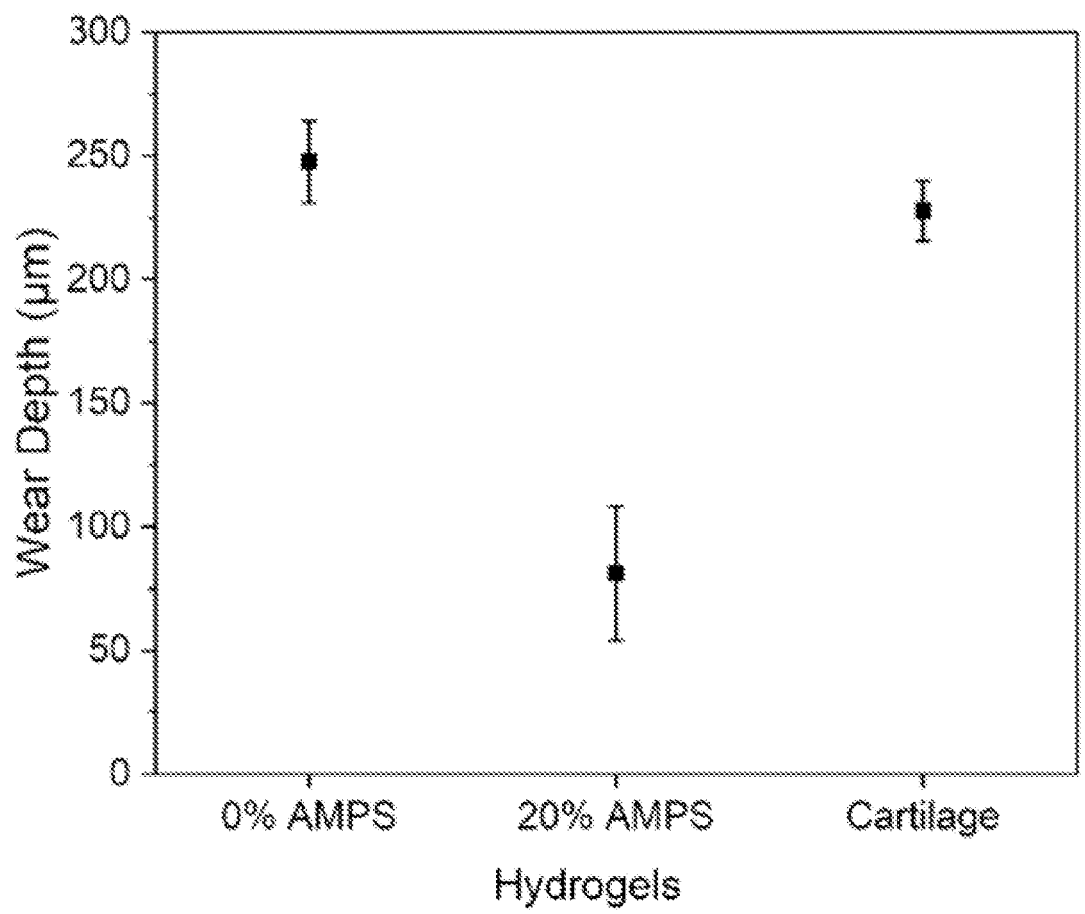
Figure 8A:
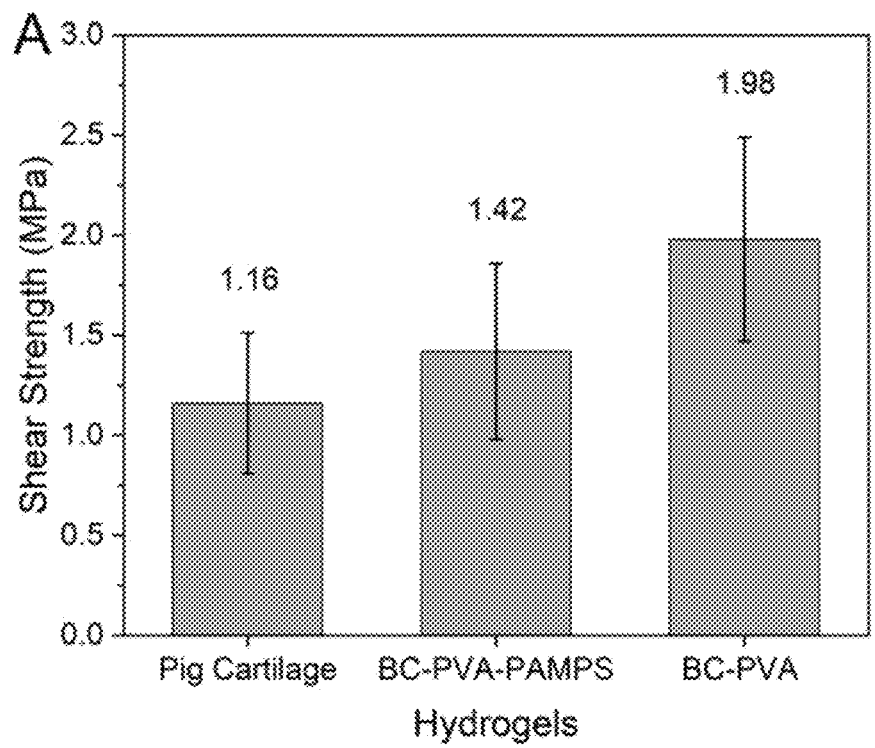
FIGS. 8A-8D illustrate various aspects of shear strength testing of various hydrogel composition and cartilage.
Figure 8B:
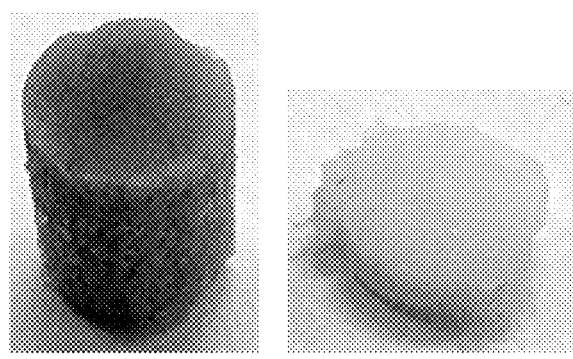
Figure 8C:
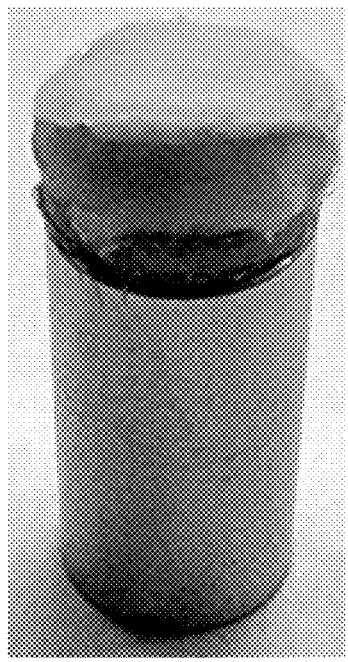
Figure 8D:
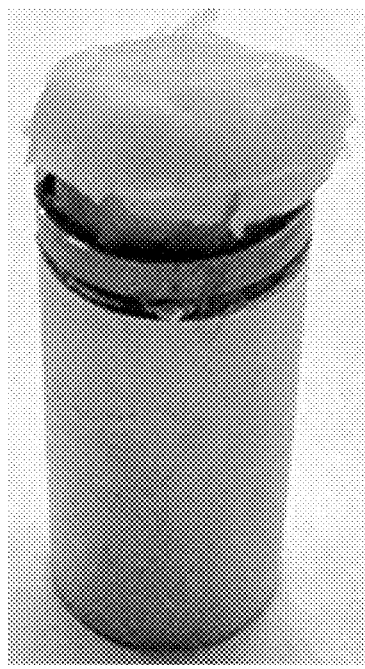

FIG. 7B shows cross-sectional Micro-CT images of the cartilage samples that were acquired in the center of the wear mark to measure the maximum wear depth. FIG. 7C compares the wear depth on cartilage caused by the hydrogels or cartilage. The wear caused by the BC-PVA on cartilage (247±16 µm) was not significantly different from the wear caused by cartilage on cartilage (228±12 µm). The addition of PAMPS into the BC-PVA reduced the wear on the opposing cartilage surface to 81±27 µm, significantly below the wear of cartilage on cartilage.

FIGS. 8A-8D show various aspects of shear strength testing of various hydrogel composition and cartilage. It was hypothesized that increasing the tensile strength of the hydrogel should also increase the shear strength. In order to be used for a cartilage replacement material, a synthetic hydrogel should be secured into a defect site with the same shear strength as the junction between cartilage and bone. One way to accomplish this goal is to have hydrogels that directly attach to bone or cartilage with sufficient strength. Alternatively, the hydrogel can be attached to a metallic base, such as titanium, which has the ability to integrate with bone. As mentioned above, the ability to attach BC-PVA-PAMPS hydrogels to a metallic base with a shear strength equivalent to the cartilage-bone interface, as described in PCT/US2021/040031. Previous tests indicated the strength of hydrogel attachment was limited by the tensile force required to fracture the hydrogel that is curved over the edge of the metallic base. Thus, increasing the tensile strength of the hydrogel should in turn increase the shear strength with which the hydrogel is attached to a metallic base.

The setup used for shear testing is described in Example 7 and 12 below. FIGS. 8A-8D show the results for shear testing a plug of porcine cartilage on bone extracted from a pig knee, testing of a BC-PVA-PAMPS hydrogel made with the previous freeze-thaw process, and testing a BC-PVA hydrogel annealed at 90° C. and then rehydrated. Both of the hydrogels are attached to stainless-steel rods with a combination of RelyX Ultimate cement and a shape memory alloy ring. The BC-PVA shear strength of 1.98 is significantly greater than that of porcine cartilage (p-value from one-way ANOVA is <0.05). The average value of the shear strength for BC-PVA is also 40% greater than that of BC-PVA-PAMPS, but the error in the measurements is such that the difference in these values is not statistically significant. Comparison of the sample after failure show that while pig cartilage was sheared completely off of the underlying bone, both BC-PVA-PAMPS (made with the freeze-thaw process) and BC-PVA (made by annealing at 90° C., followed by rehydration) were fractured on one side of the cylindrical sample but remained attached. These results show that the shear strength of attachment for the annealed BC-PVA is greater than that of pig cartilage.

Described above are tensile strength, compression strength and shear strength of BC-reinforced hydrogels attached to a metal pin with a diameter of 5.2 mm. While this size is convenient for testing, such a diameter is too small to serve as an implant for partial knee resurfacing. In addition, the samples lacked the curvature necessary to mimic the natural curvature of the femoral condyle. FIGS. 9A-9F show application of an annealed BC-PVA hydrogel on an implant for partial knee resurfacing to demonstrate the ability of the hydrogel to attach to a metal base with a size and shape representative of an implant for partial knee resurfacing.

FIGS. 9A and 9B show the implant prior to mechanical testing. The implant sample is 20 mm in diameter with a radius of curvature of 20 mm. An implant diameter of 20 mm is a typical size used for an osteochondral allograft, and a 20 mm radius of curvature is within the range of typical curvatures for the femoral condyle. The peak force on the knee during jogging has been measured to be 5551 N for a body weight of 100 kg. The tibiofemoral contact area has been measured to be 1500 mm 2 at 3100 N. The peak stress on the contacted area of the knee during jogging is 3.7 MPa based on the assumption that the contact area will not increase at a higher force. FIGS. 9C and 9D show the implant after being subjected to a compression stress of 16 MPa, 4.3 times greater than the peak physiological force on the femoral condyle. After this test, there were no signs of fracture or damage on the surface of the hydrogel. This test indicates an implant created with the annealed BC-PVA hydrogel can withstand the compressive forces in the knee without fracture. Peak anterior shear forces in the knee for walking have been measured to be 30% of body weight, or 294 N for a 100 kg individual. This is the highest shear force measured in the knee for any investigated daily activity. The tibiofemoral contact area has been measured to be 1500 mm 2 at 3100 N, which is approximately equivalent to the peak normal force during walking for an individual with a body weight of 100 kg. As the peak normal force coincides with the peak shear force, we can use this tibiofemoral contact area to calculate that the peak shear stress experienced by cartilage during walking is 0.2 MPa (294 N÷1 500 $mm^2$). Shear testing on the implant indicated failure did not occur until a stress of 0.9 MPa was applied. Since the implant can withstand shear loads 4.5 times greater than that experienced by cartilage in the knee, this result shows the annealed BC-PVA hydrogel and method of attachment have sufficient strength for creation of an implant for partial knee resurfacing.

An implant for partial knee resurfacing may be relatively large and may be curved to mimic the natural curvature of the femoral condyle. FIGS. 14A-14C shows images of an implant 20 mm in diameter with a radius of curvature of 20 mm. An implant diameter of 20 mm is a typical size used for an osteochondral allograft, and a 20 mm radius of curvature is within the range of typical curvatures for the femoral condyle. In this example, five pieces of BC were cut into shapes with 8 octagonal legs to enable the BC to fold over the edge of the implant. A 0.25-mm-thick coating of commercially pure titanium was applied to the stem of the implant and underneath the base with a plasma spray process in order to improve integration with bone. FIGS. 14B and 14C show an example of how such an implant would be used to resurface the knee. FIG. 14B shows an example of a cartilage defect. The surgeon would drill out a hole over the defect site that is complementary to the shape of the hydrogel-capped implant. The hydrogel-capped implant would then be pressed into the hole to replace the damaged cartilage.

The methods and apparatuses described herein may be used to reinforce an annealed PVA hydrogel with BC to provide, for the first time, a hydrogel with a compression and tensile strength greater than cartilage. Annealing increased the tensile strength of BC-PVA by 5 times and the compressive strength by 1.8 times relative to a freeze-thaw process due to the greater crystallization and lower water content that was achieved by annealing. Reinforcement of PVA with BC lowered the wear of the hydrogel by 4 times relative to PVA alone, and 3 times relative to cartilage. The annealed BC-PVA hydrogel caused a minimal amount of opposing surface wear, similar to what was caused by cartilage on itself. Attachment of the BC to a metal plug via an adhesive and/or clamp, followed by infiltration and annealing of the PVA, enabled attachment of the BC-PVA hydrogel to a metal backing with a shear strength greater than the attachment of cartilage to bone. These advances in hydrogel strength and attachment enable the creation of an implant with a hydrogel surface and titanium backing that can enable durable resurfacing of damaged cartilage in an articulating joint.

Figure 10A:
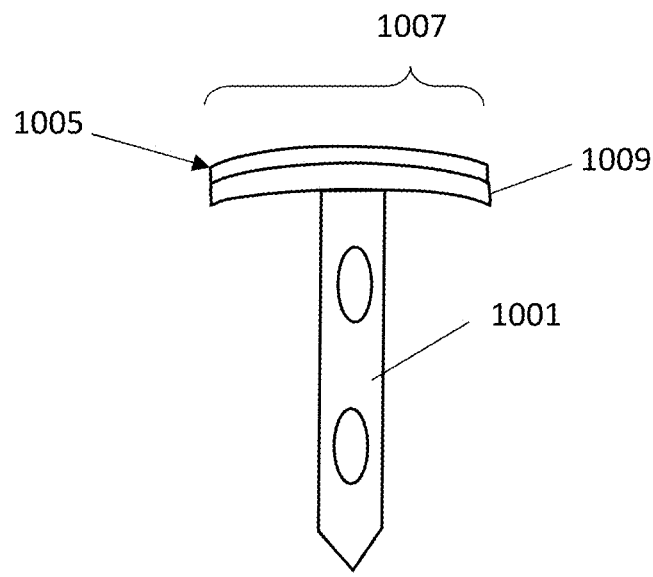
FIGS. 10A and 10B schematically illustrate examples of implants including a hydrogel attached (e.g., forming the surface) as described herein.
Figure 10B:
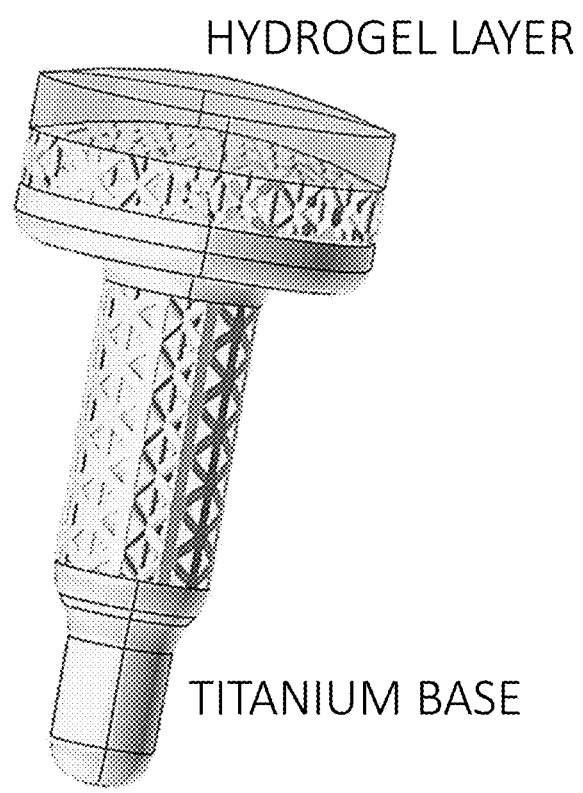

As used herein, an implant may have any appropriate structure for implanting into a body. In some (non-limiting) examples, the implants may have a shape that allows them to be implanted into bone, with a hydrogel attached to an outward-facing side. For example, FIGS. 10A and 10B illustrate examples of implants to which a hydrogel has been attached, as described herein. In FIG. 10A, the implant includes a base 1001 (e.g., a titanium base) having an elongate pin-shape that may be, for example, 2 mm×7 mm (tapering to about 1.5 mm at about 3 mm from the end). The base may include one or more channels, openings, passages, etc. for ingrowth of bone. The implant also includes a top portion 1005 that may be curved (e.g., with a single curvature or a double-curvature. For example, the surface may be curved with a radius of curvature of about 17 mm (single curvature) or about 19 mm×12 mm (double curvature). In FIG. 10A the top is approximately 7 mm in diameter 1007. The outer surface of the implant may be approximately 1 mm thick or thicker 1009 and may be about 70% porous, or greater. The hydrogel may be attached to the top surface. The hydrogel in this example is a triple-network hydrogel of BC-PVA-PAMPS and the BC is cemented to the porous top, while the PVA-PAMPS is impregnated into the BC. FIG. 10B shows a similar implant to that shown in FIG. 10A, in which a hydrogel is attached (e.g., via cementing the nanofibrous portion of the hydrogel to the porous surface of the implant, as shown. The implant in FIG. 10B is titanium.

As mentioned above, any of these implant surfaces may include a porous structure. The porosity of the implant surface may be, e.g., between 10% porous and 90% porous, e.g., between 30% and 90% porous, between 55% porous and 95% porous, between 65% porous and 85% porous, etc.). The depth of the pores may also be varied. For example, the surface may be porous to a depth of between 0.1 mm and 5 mm, between 0.2 mm to 3 mm, between 0.5 mm to 2 mm (e.g., 0.2 mm or greater, 0.3 mm or greater, 0.5 mm or greater, 0.75 mm or greater, 1 mm or greater, 1.5 mm or greater, etc.).

As mentioned, any appropriate nanofibrous network may be used, including, but not limited to nanofibrous bacterial cellulose. Other nanofibrous networks may include electrospun polymer nanofibers such as poly(vinyl alcohol) (PVA) nanofibers, aramid nanofibers (e.g., Aramid-PVA nanofibers), wet-spun silk protein nanofiber, chemically cross-linked cellulose nanofiber, or polycaprolactone fibers (e.g., 3D woven PCL fibers). In addition, any appropriate double network hydrogels may be used, including but not limited to PVA and PAMPS. For example, other hydrogel-forming polymers may include poly-(N,N'-dimethyl acrylamide) (PDMAAm), copolymers of 1-vinylimidazole and methacrylic acid, double-network hydrogels based on amphiphilic triblock copolymers, polyampholyte hydrogels, a PVA-tannic acid hydrogel, a poly(N-acryloyl) glycinamide hydrogel, polyacrylic acid-acrylamide-C18 hydrogel, Guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-$Fe^{3+}$-chitosan hydrogel, a poly(methacrylic acid) gel, a Graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, a Agar-poly-hydroxyethylmethacrylate gel, a polyfacryloyloethyltrimethylammonium chloride hydrogel, a poly(3-(methylacryloylamino)propyl-trimethylammonium chloride hydrogel, a poly(sodium p-styrenbesulfonate) hydrogel, a polyethylene glycol diacrylate hydrogel, a polyethylene glycol hydrogel, or hydrogels composed of a combination of these polymers.

The implants described herein may be formed of any appropriate material, including, but not limited to titanium and stainless steel. For example, a hydrogel may be attached as described herein to an implant surface (e.g., base, including a porous base) that is formed of a stainless steel alloy, other titanium alloys, Co—Cr alloys, tantalum, gold, niobium, bone, Al oxide, Zr oxide, hydroxyapatite, tricalcium phosphate, calcium sodium phosphosilicate (Bio glass), poly(methyl methacrylate), polyether ether ketone, polyethylene, polyamide, polyurethane, polytetrafluoroethylene, or other materials used for making implants.

Any of the implants described herein may include a hydrogel having a surface that is substantial smooth and/or is shaped in a predetermined configuration, such as (but not limited to) concave, convex, saddle-shaped, etc. For example, any of these apparatuses (e.g., implants) may have a surface roughness that is less than 30 microns. In some cases, the surface may be formed smooth by molding. In some cases, the surface may be formed smooth by polishing or sanding. For example, once the additional hydrogel components have formed the network (e.g., the nanofibrous-reinforced network), the hydrogel coating may optionally be finished by polishing; in particular, the surface may be sanded to polish to a roughness of less than 30 microns. Polishing may be performed by sanding (e.g., using a fine grit sanding surface, such as a 600, 400, 320, etc. grit).

Figure 11:
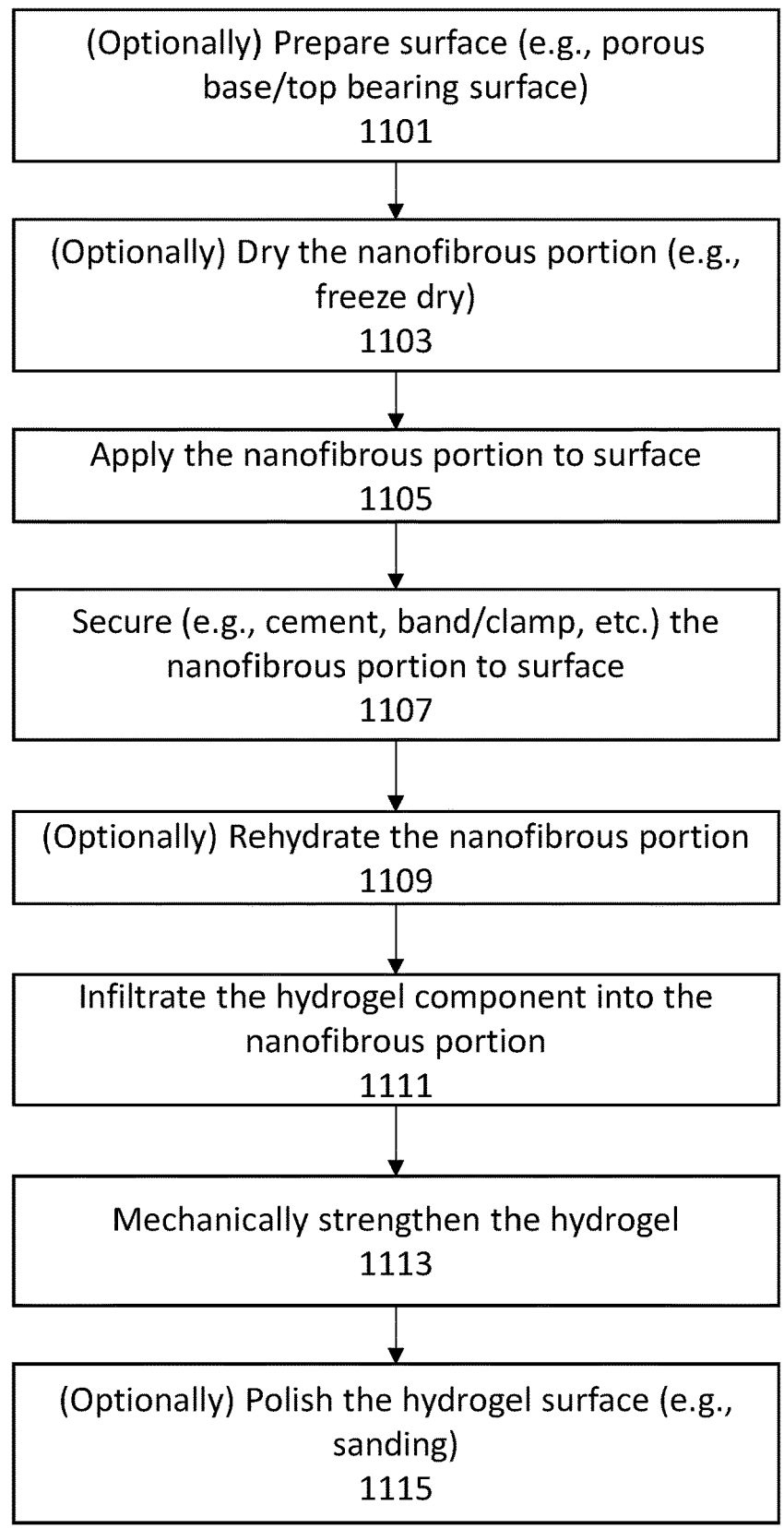
FIG. 11 illustrates an exemplary method of forming and attaching a hydrogel surface.
Figures 15A, 15B, 15C, 15D:
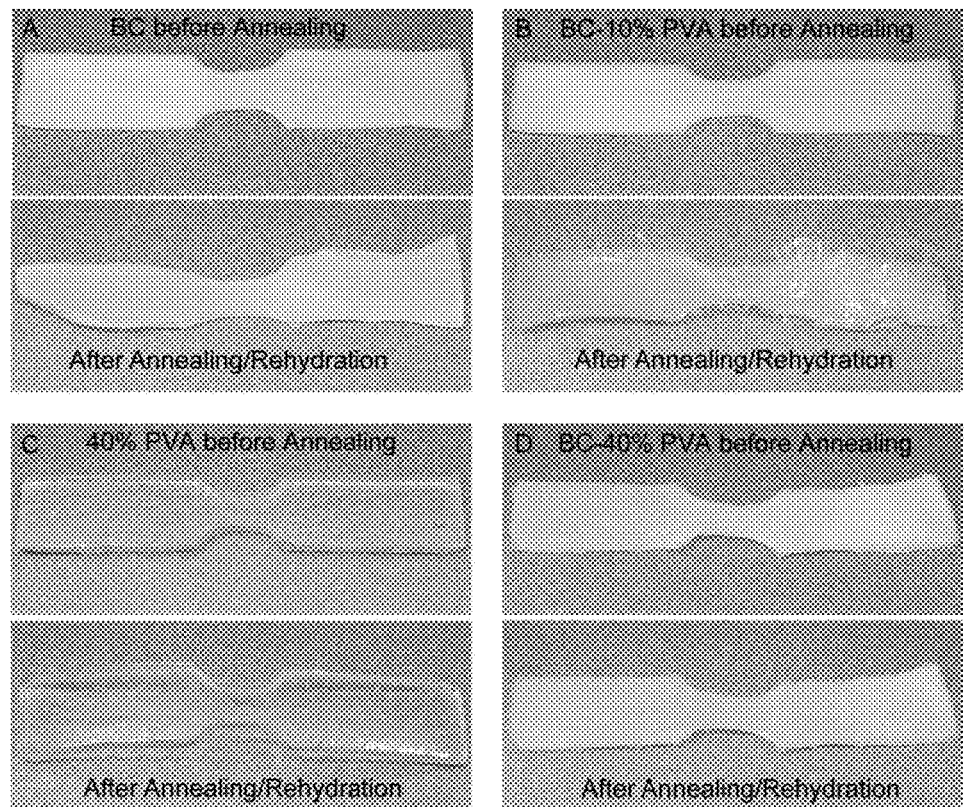
FIGS. 15A-15D show hydrogel samples before and after annealing and rehydration. All samples were annealed at 90° C. for 25 hours and rehydrated in PBS solution for 24 hours at 23° C. (A) A sample of BC without PVA. (B) A sample of BC that was annealed in a solution of 10 wt. % PVA. (C) A sample of 40 wt. % PVA. (D) A BC sample that was infiltrated with 40 wt. % PVA in a hydrothermal bomb for 24 hours at 120° C. before annealing and rehydration.

FIG. 11 is a flowchart illustrating an exemplary method of making an apparatus as described herein. The surface to which the hydrogel is to be attached, e.g., an implant surface, may optionally be prepared 1101. For example, the surface may be made porous. In some examples, the porosity may be at least 0.5 mm deep (e.g., 1 mm deep or deeper). The porosity may be described as the percent porosity (e.g., between 10% and 90% porous, between 20% and 90%, greater than 30%, greater than 40%, greater than 50%, etc.).

The nanofibrous portion may then be prepared for attachment to the surface 1103. For example, the nanofibrous portion dried (e.g., freeze dried). The nanofibrous portion may be applied dry or substantially dry, to the attachment surface 1105. The nanofibrous portion may then be secured to the surface 1107. In some variations an adhesive (e.g., cement) may be applied to the surface before the nanofibrous portion is applied and/or the adhesive may be applied onto the nanofibrous portion on the surface. In some variations the adhesive may be applied to the nanofibrous portion prior to attaching to the surface. In some examples an adhesive is not used at all.

The adhesive, if used, may be applied to dry (e.g., for a predetermined time, e.g., 1 hour, 2 hours, 3 hours, 6 hours, 12 hours, 24 hours, etc.) at a drying temperature (e.g., room temperature, 30 degrees, etc.). Once dried, the nanofibrous portion that is cemented to the surface may optionally be rehydrated 1109, e.g., by the addition of an aqueous solution.

The nanofibrous portion may then be infiltrated by the other components of the hydrogel, which become impregnated into the nanofibrous portion secured onto the surface 1111. The other components may include one or more polymer components capable of forming a hydrogel and that are crystallizable upon a subsequent annealing process. In some examples, the polymer components include polyvinyl alcohol (PVA). In some examples, the polymer component only includes PVA.

Once the polymer hydrogel component is infused within the nanofibrous portion, a mechanical strengthening process may be implemented to strengthen the hydrogel. The mechanical strengthening process may include drying, annealing and rehydrating the hydrogel. Drying and/or annealing may include heating the hydrogel to a predetermined temperature (e.g., ranging from 90° C. to 140° C.), followed by rehydration (e.g., in PBS solution). The resulting hydrogel may have an increased crystalline structure. For example, the interstitial polymer hydrogel (e.g., PVA) may have a crystallinity of at least 20%. In some examples, the tensile strength of the resulting hydrogel is at least 40 MPa. In some examples, the compressive strength of the resulting hydrogel is at least 59 MPa. In addition, the hydrogel may have a water content of about 20 wt % or greater. Once the mechanical strengthening process is complete, the hydrogel surface may optionally be polished 1115.

In some examples the apparatuses described herein may form part of a surgical implant for treating a defect, such as an osteochondral defect. For example, a surgical implant may include a surface that is covered in a hydrogel; this surface may act an interface between one or more other body regions, including hard tissues, such as bone and cartilage. Repair of a cartilage lesion with a hydrogel may benefit from long-term fixation of the hydrogel in the defect site. Attachment of a hydrogel to a base (substrate) that allows for integration with bone could enable long-term fixation of the hydrogel, but current methods of forming bonds to hydrogels have less than a tenth of the shear strength of the osteochondral junction. The apparatuses and methods described herein may include bonding a hydrogel to a surface (e.g., base) with a shear strength that is many times larger than has been previously achieved.

FIGS. 12A-12C illustrate a brief overview of an example of how the hydrogel may be attached to a metal base (e.g., of the top bearing surface). In this example freeze-dried BC sheets were cut into octagonal shapes with 8 projections (e.g., "legs") that can be bent over the edges of the implant, as shown in the example of FIG. 12D. This cut may remove excess BC that would otherwise be folded up on the sides of the cylinder. The pieces of cut BC were then placed into a fixture that facilitates centering and alignment of the ring clamp with the pieces of BC and the metal rod. The metal rod was pushed down through the fixture so that the ring pushed the pieces of BC onto the metal rod. This process of pushing the ring over the BC and onto the rod could also be done by hand. The use of an alignment features, such as shown in FIGS. 12B-12C may help consistently center the pieces during assembly. The sample may then be clamped, e.g., by heated in an oven at 90° C. to initiate clamping in a shape-memory alloy material preset as described herein (which starts at a temperature of 50° C.). The part was then heated in a hydrothermal bomb at 120° C. for 24 hours with PVA to infiltrate the polymer into the BC. The part was then dried, annealed, and rehydrated as described herein.

The following are example methods for preparing and testing various hydrogel samples described herein.

Example 1: Fabrication of BC-PVA-PAMPS Hydrogel

BC sheets were pressed to be 0.5 mm thick and placed into a hydrothermal reactor with a mixture of polyvinyl alcohol (PVA) (40 wt. %) and deionized water (60 wt. %). The hydrothermal reactor was sealed and heated at 120° C. for 24 hours to allow the PVA to diffuse into the voids of BC and form a BC-PVA hydrogel. The BC-PVA hydrogel was removed from the reactor when hot (e.g., greater than 85° C.). The residual PVA solution was removed by scrapping the surface of the BC-PVA samples with a metal spatula. The samples were frozen at −78° C. for 30 minutes and thawed at room temperature to physically crosslink the PVA network. The BC-PVA hydrogel was then soaked in a solution of 2-acrylamido-2-methylpropanesulfonic acid sodium salt (AMPS) (30 wt. %), N,N'-methylenediacrylamide (MBAA) (60 mM), 2-hydroxy-4'-(2-hydroxyethoxy)-2-methylpropiophenone (12959) (50 mM) and potassium persulfate (KPS) (0.5 mg mL-1) for 24 hours. The hydrogel was cured with an ultraviolet (UV) transilluminator for 15 minutes on each side, and further cured in an oven at 60° C. for 8 hours to ensure even and complete curing. The resulting BC-PVA-PAMPS hydrogel was stored in phosphate buffered saline (PBS) for at least 24 hours before further characterization.

Example 2: Fabrication of Annealed BC

BC sheets were pressed to be 0.5 mm thick. The BC sheets were then placed into a 90° C. oven for 24 hours before being annealed at 90° C. for an additional hour. The resulting annealed BC was cut into the desired shape and stored in 0.15 M PBS for at least 24 hours.

Example 3: Fabrication of PVA Hydrogel

To fabricate the PVA hydrogel, a slurry of PVA (40 wt. %) and DI water (60 wt. %) were mixed in a metal baking pan (diameter: 203.2 mm) and heated at 120° C. for 20 minutes in an autoclave sterilizer. To make annealed PVA hydrogel, the resulting hydrogel was dried in an oven at 90° C. for 24 hours before being annealed at 90° C., 120° C. or 140° C. for an additional hour. To make freeze-thawed PVA hydrogel, the autoclaved hydrogel was frozen at −80° C. for 30 minutes and thawed at 23° C. for 30 minutes. The resulting PVA hydrogel was cut into the desired shape and stored in 0.15 M PBS for at least 24 hours before tests.

Example 4: Fabrication of Annealed BC-40 wt. % PVA Hydrogel

BC sheets were pressed to be 0.5 mm thick and placed into a hydrothermal reactor with a mixture of PVA (40 wt. %) and DI water (60 wt. %). The hydrothermal reactor was sealed and heated at 120° C. for 24 hours to allow the PVA to diffuse into the voids of BC and form a BC-PVA hydrogel. The BC-PVA hydrogel was removed from the reactor when hot (e.g., greater than 85° C.). Note the hydrothermal reactor was pressurized with hot steam and created a burn hazard, so personal protective equipment including lab coat, heat resistant gloves and full-coverage face shields should be used when opening the reactor. The residual PVA solution was removed by scrapping the surface of the BC-PVA samples with a metal spatula. The samples were dried in an oven at 90° C. for 24 hours before annealing at 90° C., 120° C. or 140° C. for an additional hour. The resulting annealed BC-PVA hydrogel was cut into a desired shape and stored in 0.15 M PBS for at least 24 hours before tests.

Example 5: Fabrication of Annealed BC-10 wt. % PVA Hydrogel

BC sheets were pressed to be 0.5 mm thick and placed into a baking pan (15.6 cm×8.6 cm×4.2 cm). Approximately 30 mL of 10 wt. % PVA solution was added to the baking pan. The baking pan was placed in an oven at 90° C. for 24 hours and annealed at 90° C. for an additional hour. The resulting annealed BC-PVA hydrogel was cut into the desired shape and stored in 0.15 M PBS for at least 24 hours.

Example 6: Fabrication of Annealed BC-PVA-PAMPS Hydrogel

BC sheets were pressed to be 0.5 mm thick and placed into a hydrothermal reactor with a mixture of PVA (40 wt. %) and DI water (60 wt. %). The hydrothermal reactor was sealed and heated at 120° C. for 24 hours to allow the PVA to diffuse into the voids of BC and form a BC-PVA hydrogel. The BC-PVA hydrogel was removed from the reactor when hot (>85° C.). Note the hydrothermal reactor was pressurized with hot steam and created a burn hazard, so personal protective equipment including a lab coat, heat resistant gloves and full-coverage face shields should be used when opening the reactor. The residual PVA solution was removed by scrapping the surface of the BC-PVA samples with a metal spatula. The samples were dried in an oven at 90° C. for 24 hours before being annealing at 90° C., 120° C. or 140° C. for an additional hour. The annealed BC-PVA hydrogel was then soaked in a solution of AMPS (30 wt. %), MBAA (60 mM), 12959 (50 mM) and KPS (0.5 mg mL-1) for 24 hours. The hydrogel was cured with a UV transilluminator (VWR International) for 15 minutes on each side, and further cured in an oven at 60° C. for 8 hours to ensure even and complete curing. The resulting annealed BC-PVA-PAMPS hydrogel was stored in PBS for at least 24 hours before further characterization.

Example 7: Fabrication of Hydrogel on the Stainless-Steel Pin

Preparation of all hydrogel samples started with cutting the freeze-dried BC. The BC is cut in the shape of an octagon with diameter D and 8 legs which has leg length of L and widths of W=0.383D (See FIGS. 2A-2D, for example). The sample was labeled as BC-D-L after cutting. The 8-piece star shape (BC-D-L) was generated by MATLAB and loaded into Adobe Illustrator. In Adobe Illustrator the stroke of the shape is changed to 0.0001 pt to ensure accurate cutting. The file is sent to the laser cutter (Epilog Fusion M2) by using the print function and the laser cutter was selected as the printer. The vector process is used, with 100% speed, 20% power and 100% frequency. For cutting the BC, a clean metal plate was placed on the bed of the laser cutter, and the freeze-dried BC was placed on onto the metal plate. Another metal plate was placed onto the edge of the BC to ensure the BC stays in place. The focus was adjusted, and the shape was cut by the machine. After cutting, the BC was collected and stored in a petri dish for future use.

For preparing the shear test samples, six pieces of BC were adhered to the stainless-steel rod with one layer of cement and a clamp. An overview of the assembly method is shown in FIGS. 12A-12C and 13. A stainless-steel test rod was machined to have a top section with a diameter of 5.2 mm and a height of 2 mm, and a bottom section with a diameter of 6.75 mm and a height of 13 mm. Three pieces of BC-6.5-2.25 and 3 pieces of BC-6.5-2 were placed in an alignment fixture. As an optional step an adhesive (e.g., Scotchbond Universal Adhesive) may be applied to the layer of the BC in contact with the rod and the top surface of the rod. If used, the adhesive was allowed to set for 20 seconds before being blown by air for another 5 seconds. In one example, about 0.15 g of RelyX Ultimate Cement was then applied to the same surfaces coated with the Scotchbond Universal Adhesive. The rod was pressed into the BC layers and then into a shape memory alloy ring clamp. The cement was cured for 1 h. The sample was heated in an oven at 175° C. for 10 min to shrink the clamp. The sample was then soaked in DI water for 1 hour in a centrifuge tube before future use. The sample with BC on top then went through the specific hydrogel fabrication process.

Compression test samples were fabricated using the stainless-steel rod and a clamp, but without cement. Wear test samples were fabricated with a stainless-steel rod 5.7 mm in diameter and 38 mm in height, 3 pieces of BC-6.5-2, and the shape memory alloy ring, but without cement.

Example 8: Monotonic Tensile and Compression Tests

Monotonic tensile tests were carried out on an Instron 1321 (Instron, Norwood, MA, USA) and a TestResources 830 (TestResources, Shakopee, MN, USA) load frame at a rate of 0.25 mm s$^{-1}$. The finished hydrogel was cut into an ASTM D638-14 Type V shape with a titanium hollow punch for testing (see FIG. 1 for examples). The dimensions of the samples were measured with a caliper before testing. The ultimate tensile strength (UTS) was the maximum stress measured before fracture in the case of the BC-PVA samples, or the maximum compressive stress at 80% strain for the PVA samples. The tensile modulus was taken as the slope of the stress-strain curve at a stress of 1 MPa for comparison with previous studies of human cartilage.

The compressive properties of all samples were measured with an axial Torsion System (TestResources 830LE63). Cylindrical samples of PVA were cut out of films of hydrogel with a hollow steel punch with a diameter of 4 mm. BC-PVA samples were attached to a metal pin for compression testing in order to have a sample that was sufficiently thick. The dimensions of the samples were measured with a caliper before testing. The compressive properties were measured with a strain rate of 0.05 s$^{-1}$. The ultimate compressive strength was taken as the maximum stress measured before fracture. The compressive modulus was derived as the slope of the stress-strain curve at a stress of 0.4 MPa for comparison with previous studies of human cartilage.

Example 9: Differential Scanning Calorimetry

Differential scanning calorimetry (DSC) was performed on hydrogels to determine the crystallinity of the PVA. The tests were completed on a TA TGA550. In a typical experiment, a hydrogel sample of approximately 5 mg was placed in an aluminum pan under a nitrogen gas flow and heated at a rate of 10° C./min from 25° C. to 300° C. Typical thermograms for PVA, BC-PVA and BC-PVA-PAMPS hydrogels are shown in FIGS. 4A-4D.

The calculation for how much of the PVA was crystallized, i.e., the degree of crystallinity, was adopted from Hassan et al.22 After the DSC thermogram was acquired, the area under the melting peak over the range 140-220° C. (as shown in FIGS. 5A and 5B) was integrated to obtain a value with units of J·° C.·S-1·g-1. This number was then divided by the heating rate (0.17° C.·S$^{-1}$) to obtain ΔH (J·g$^{-1}$). The crystallinity of PVA was then calculated by dividing ΔH for the sample by the heat required for melting a 100% crystalline PVA sample, ΔH$_c$=138.6 J/g, and the weight fraction of PVA in the sample, w$_{PVA}$, $$X_{PVA} = \frac{\Delta H}{w_{PVA} \times \Delta H_c}$$

where $\chi_{PVA}$ is the crystallinity of the PVA.

Example 10: Measurement of Solid Weight Fraction

The weight of approximately 1 g of hydrated hydrogel was measured before drying at 90° C. for 24 hours. The weight of the dehydrated sample was then measured. The weight after dehydration was divided by the weight before dehydration to determine the solid weight fraction of the hydrogel sample.

Example 11: Wear Testing

The wear resistance of the hydrogels and porcine cartilage samples were determined with the pin-on-disk setup shown in FIGS. 6A-6D. The pin-on-disk method was used with an Anton Paar Rheometer (MR302) and a tribology accessory (SCF7). Cartilage samples were harvested from pig femurs with an osteochondral autograft transfer system (Arthrex). The femurs were purchased from a local grocery store and frozen at −78° C. before harvesting the samples. Hydrogel samples were polished with #600, #800, #1000, #1200, #1500, #2000, #2500 and #3000 sandpapers to make them smooth prior to testing. A hydrogel pin was fabricated by using the method described in Example 7 above. A disk of hydrogel or porcine cartilage with a diameter of 12.7 mm was adhered with cyanoacrylate glue (Gorilla Glue Company) to the sample holder. The testing parameters were as follows: 1,000,000 rotations; angular speed: 319 rounds per minute (maximum linear velocity: 100 mm s-1); normal force: 28.26 N (pressure: 1 MPa). A pressure of 1 MPa was applied to each sample for 5 minutes before tests started. The tests were performed in FBS. FBS is often used during wear tests to mimic the lubrication provided by synovial fluid.

After the wear test, the samples were rehydrated in FBS for 24 hours to allow the gels to recover from the applied pressure before the wear depth was measured with a High-Resolution X-ray Computed Tomography (Micro-CT) Scanner (Nikon XTH 225 ST). A 3D model of the reconstructed Micro-CT images was rendered with Avizo 9 Lite. To measure the wear depth, a slice of the 3D model was taken in the middle of the wear mark. The wear depths were measured from the images of the middle slices with ImageJ.

For calculating the COF, we determined the total friction force (F) from the torque (T) and the radius of the pin in the pin-on-disk setup (R):

$$F = \frac{3T}{2R}$$

The COF can then be calculated by:

$$COF = \frac{F}{F_N}$$

Here $F_N$ is the normal force (28.26 N). The linear velocity (v) was calculated by:

$$v = \omega R$$

where ω was the angular speed of the pin.

The results described above are particularly and unexpectedly surprising, showing that annealed BC-PVA as described herein provide a material that maintains a low coefficient of friction (0.21) over 1 million or more cycles of wear that is similar to cartilage (0.2). In contrast, annealed PVA by itself has a COF that increases from 0.033 to 0.135 over the million cycles. It is particularly surprising that adding the BC to the PVA resulted in a long-term COF that is 6.5 times lower than PVA by itself. This lower COF enabled by BC is critical to preventing wear of an opposing cartilage surface. Along the same lines, it is surprising that adding BC to annealed PVA decreased the wear depth by more than three times relative to annealed PVA by itself. This greater wear resistance enabled by BC may also be critical for the long term durability of the implant.

Example 12: Shear Testing

Shear testing was performed on an 830LE63 Axial Torsion Test Machine equipped with a 100 pound (lb) load cell. Each test was performed in a customized shear test fixture (see FIG. 13). For shearing of cartilage or hydrogel on metal samples, the sample was secured in a cylindrical hole in the left side of the fixture. The hole size was 6 mm for the pig plug and 7 mm for the hydrogel samples. Spacers were added underneath the samples to precisely align the shear plane to the cartilage-bone or hydrogel-metal interface. The right side of the fixture was machined to have a complementary half-cylinder that was used to push the hydrogel or cartilage off of their substrates. The diameter of the right half-cylinder matched that of the left side (either 6 or 7 mm). Rubber was placed between the sample and the right shear fixture to apply pressure during the shear test in order to minimize cleavage and peeling. A crosshead displacement rate of 2 mm min-1 was used for all the measurements.

Supplemental Materials

As mentioned, in some of these examples, Bacterial Cellulose (BC) was purchased from Gia Gia Nguyen Co. Ltd. Poly(vinyl alcohol) (PVA) (fully hydrolyzed, molecular weight: 145,000 g mol$^{-1}$), N,N'-methylenediacrylamide (MBAA, 97.0%), 2-hydroxy-4'-(2-hydroxyethoxy)-2-methylpropiophenone (12959), potassium persulfate (KPS) and 2-acrylamido-2-methylpropanesulfonic acid sodium salt (AMPS, 50 wt. % solution in water) were purchased from Sigma Aldrich. Phosphate buffered saline (PBS) was purchased from VWR International. Fetal bovine serum (FBS, Canada origin, collected from cattle typically 12-24 months old) was purchased from Corning. Shape memory alloy ring clamps were purchased from Intrinsic Devices.

In some examples, BC sheets were pressed to be 0.5 mm thick and placed into a hydrothermal reactor with a mixture of PVA (40 wt. %) and DI water (60 wt. %). The hydrothermal reactor was sealed and heated at 135° C. for 24 hours to allow the PVA to diffuse into the voids of BC and form a BC-PVA hydrogel. The BC-PVA hydrogel was removed from the reactor when hot (>85° C.). Note the hydrothermal reactor was pressurized with hot steam and is a burn hazard, so personal protective equipment including lab coat, heat resistant gloves and full-coverage face shields should be used when opening the reactor. The residual PVA solution was removed by scrapping the surface of the BC-PVA samples with a metal spatula. The samples were frozen at −78° C. for 30 minutes and thawed at room temperature to physically crosslink the PVA network. The BC-PVA hydrogel was then soaked in a solution of AMPS (30 wt. %), MBAA (60 mM), 12959 (50 mM) and KPS (0.5 mg mL-1) for 24 hours. The hydrogel was cured with a UV transilluminator (VWR International) for 15 minutes on each side, and further cured in an oven at 60° C. for 8 hours to ensure even and complete curing. The resulting BC-PVA-PAMPS hydrogel was stored in PBS for at least 24 hours before further characterization.

As mentioned, BC sheets were pressed, e.g., to be about 0.5 mm thick. In some examples, the BC sheets were then placed into a 90° C. oven for 24 hours before being annealed at 90° C. for an additional hour. The resulting annealed BC was cut into the desired shape and stored in PBS (0.15 M) for at least 24 hours.

Any appropriate method may be used to fabricate the PVA hydrogel. For example, to fabricate a PVA hydrogel, a slurry of PVA (40 wt. %) and DI water (60 wt. %) were mixed in a metal baking pan (diameter: 203.2 mm) and heated at 120° C. for 20 minutes in an autoclave sterilizer. To make annealed PVA hydrogel, the resulting hydrogel was dried in an oven at 90° C. for 24 hours before being annealed at 90° C., 120° C. or 140° C. for an additional hour. To make freeze-thawed PVA hydrogel, the autoclaved hydrogel was frozen at −80° C. for 30 minutes and thawed at 23° C. for 30 minutes. The resulting PVA hydrogel was cut into the desired shape and stored in PBS (0.15 M) for at least 24 hours before testing.

Annealed BC-40 wt. % PVA Hydrogel may be fabricated in any appropriate manner. For example, BC sheets may be pressed to be 0.5 mm thick and placed into a hydrothermal reactor with a mixture of PVA (40 wt. %) and DI water (60 wt. %). The hydrothermal reactor was sealed and heated at 135° C. for 24 hours to allow the PVA to diffuse into the voids of BC and form a BC-PVA hydrogel. The BC-PVA hydrogel was removed from the reactor when hot (>85° C.). The residual PVA solution was removed by scrapping the surface of the BC-PVA samples with a metal spatula. The samples were dried in an oven at 90° C. for 24 hours before annealing at 90° C., 120° C. or 140° C. for an additional hour. The resulting annealed BC-PVA hydrogel was cut into a desired shape and stored in PBS (0.15 M) for at least 24 hours before tests.

In some examples Annealed BC-10 wt. % PVA Hydrogel was fabricated by pressing BC sheets to be about 0.5 mm thick and placed into a baking pan (15.6 cm×8.6 cm×4.2 cm). Approximately 30 mL of 10 wt. % PVA solution was added to the baking pan. The baking pan was placed in an oven at 90° C. for 24 hours and annealed at 90° C. for an additional hour. The resulting annealed BC-PVA hydrogel was cut into the desired shape and stored in PBS (0.15 M) for at least 24 hours.

Annealed BC-PVA-PAMPS Hydrogel was fabricated by pressing BC sheets to be about 0.5 mm thick and placed into a hydrothermal reactor with a mixture of PVA (40 wt. %) and DI water (60 wt. %). The hydrothermal reactor was sealed and heated at 120° C. for 24 hours to allow the PVA to diffuse into the voids of BC and form a BC-PVA hydrogel. The BC-PVA hydrogel was removed from the reactor when hot (>85° C.). Note the hydrothermal reactor was pressurized with hot steam and created a burn hazard, so personal protective equipment including a lab coat, heat resistant gloves and full-coverage face shields should be used when opening the reactor. The residual PVA solution was removed by scrapping the surface of the BC-PVA samples with a metal spatula. The samples were dried in an oven at 90° C. for 24 hours before being annealing at 90° C., 120° C. or 140° C. for an additional hour. The annealed BC-PVA hydrogel was then soaked in a solution of AMPS (30 wt. %), MBAA (60 mM), 12959 (50 mM) and KPS (0.5 mg mL-1) for 24 hours. The hydrogel was cured with a UV transilluminator (VWR International) for 15 minutes on each side, and further cured in an oven at 60° C. for 8 hours to ensure even and complete curing. The resulting annealed BC-PVA-PAMPS hydrogel was stored in PBS (0.15 M) for at least 24 hours before further characterization.

Fabrication of Hydrogel on a Stainless-Steel Pin

In some examples, Preparation of hydrogel samples on a stainless-steel pin started with cutting the freeze-dried BC. The BC was cut in the shape of an octagon with diameter D, 8 legs of length of L, and widths of W=0.383D. The sample was labeled as BC-D-L after cutting. The 8-piece star shape (BC-D-L) was generated by MATLAB and loaded into Adobe Illustrator. In Adobe Illustrator the stroke of the shape was changed to 0.0001 pt to ensure accurate cutting. The file was sent to the laser cutter (Epilog Fusion M2) using the print function and the laser cutter was selected as the printer. The vector process was used, with 100% speed, 20% power and 100% Frequency. For cutting the BC, a clean metal plate was placed on the bed of the laser cutter, and the freeze-dried BC was placed onto the metal plate. Another metal plate was placed onto the edge of the BC to ensure the BC did not move. The focus was adjusted, and the shape was cut by the machine. After cutting, the BC was collected and stored in a petri dish for future use.

For preparing the shear test samples, six pieces of BC were adhered to the stainless-steel rod with one layer of cement and a clamp. A stainless-steel test rod was machined to have a top section with a diameter of 5.2 mm and a height of 2 mm, and a bottom section with a diameter of 6.75 mm and a height of 13 mm. Three pieces of BC-6.5-2.25 and 3 pieces of BC-6.5-2 were placed in an alignment fixture. Scotchbond Universal Adhesive was applied to the layer of the BC in contact with the rod and the top surface of the rod. The adhesive was allowed to set for 20 seconds before being blown by air for another 5 seconds. About 0.15 g of RelyX Ultimate Cement was then applied to the same surfaces coated with the Scotchbond Universal Adhesive. The rod was pressed into the BC layers and then into a shape memory alloy ring clamp. The cement was cured for 1 h. The sample was heated in an oven at 175° C. for 10 min to shrink the clamp. The sample was then soaked in DI water for 1 hour in a centrifuge tube before future use. The sample with BC on top then went through the specific hydrogel fabrication process.

Compression test samples were fabricated using the stainless-steel rod and a clamp, but without cement. Wear test samples were fabricated with a stainless-steel rod 5.7 mm in diameter and 38 mm in height, 3 pieces of BC-6.5-2, and the shape memory alloy ring, but without cement.

Monotonic tensile tests were carried out on an Instron 1321 load frame (Instron, Norwood, MA, USA) and a Test Resources 830LE63 Axial Torsion Test Machine (TestResources, Shakopee, MN, USA) at a rate of 0.25 mm s$^{-1}$. The finished hydrogel was cut into an ASTM D638-14 Type V shape with a titanium hollow punch for testing (see FIGS. 15A-15D, for examples). The dimensions of the samples were measured with a caliper before testing. The ultimate tensile strength (UTS) was the maximum stress measured before fracture in the case of the BC-PVA samples, or the maximum compressive stress at 80% strain for the PVA samples. The tensile modulus was taken as the slope of the stress-strain curve at a stress of 1 MPa for comparison with previous studies of human cartilage.

The compressive properties of all samples were measured with a Test Resources 830LE63 Axial Torsion Test Machine. Cylindrical samples of PVA were cut out of films of hydrogel samples with a hollow steel punch with a diameter of 4 mm. BC-PVA samples were attached to a metal pin for compression testing in order to have a sample that was sufficiently thick. The dimensions of the samples were measured with a caliper before testing. The compressive properties were measured with a strain rate of 0.05 s$^{-1}$. The compressive strength was taken stress at a strain of 0.8, or the stress at fracture if the material failed before a strain of 0.8. The compressive modulus was derived as the slope of the stress-strain curve at a stress of 0.4 MPa for comparison with previous studies of human cartilage.

Figure 17A:
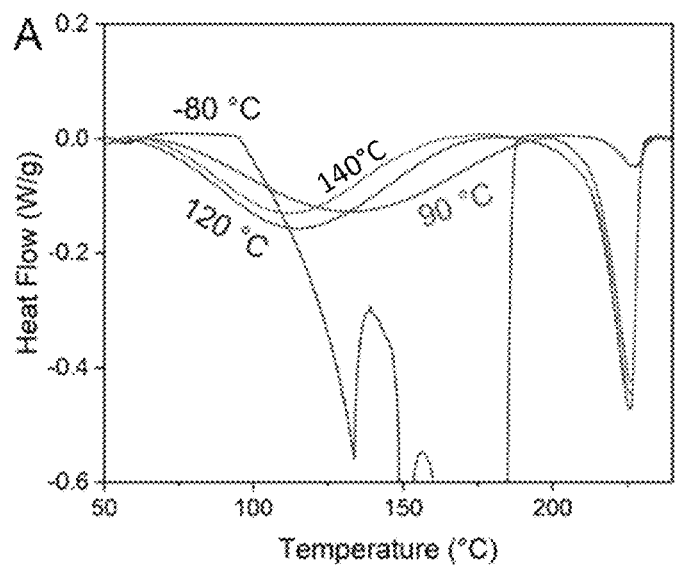
FIGS. 17A-17C show DSC thermograms for (A) freeze-thawed and annealed PVA hydrogels, (B) freeze-thawed and annealed BC-PVA hydrogels, and (C) annealed BC-PVA and annealed BC-PVA-PAMPS. The concentration of the AMPS solution used to make the BC-PVA-PAMPS was 10 wt. %.
Figure 17B:
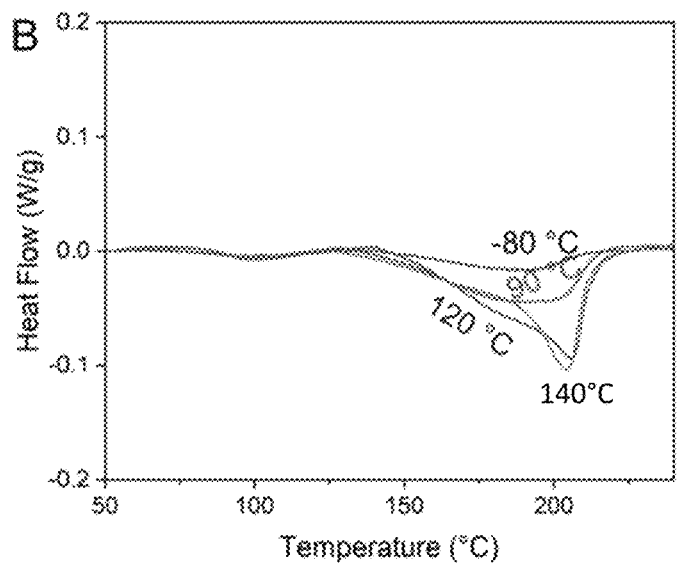
Figure 17C:
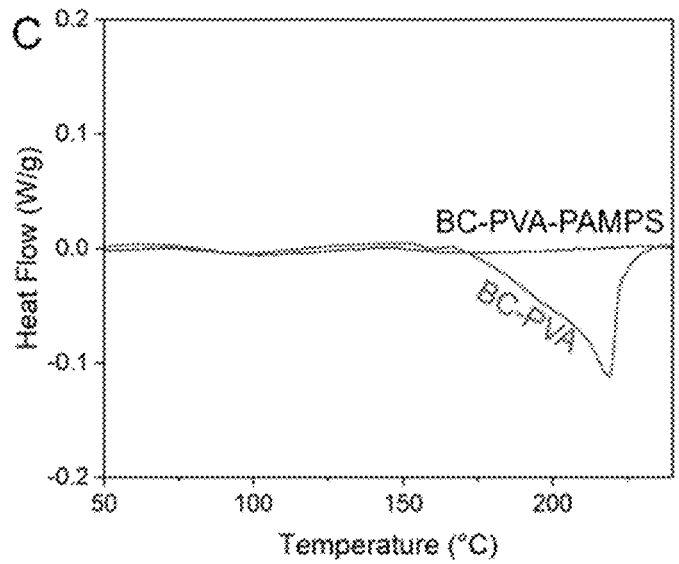

Differential scanning calorimetry (DSC) was performed on hydrogel samples to determine the crystallinity of the PVA. The tests were completed on a TA Instruments TGA550. In a typical test, a hydrogel sample of approximately 5 mg was placed in an aluminum pan and heated at a scanning rate of 10° C./min under a nitrogen gas flow from 25° C. to 300° C. Typical thermograms for PVA, BC-PVA and BC-PVA-PAMPS hydrogels are shown in FIGS. 17A-17C.

Figure 18:
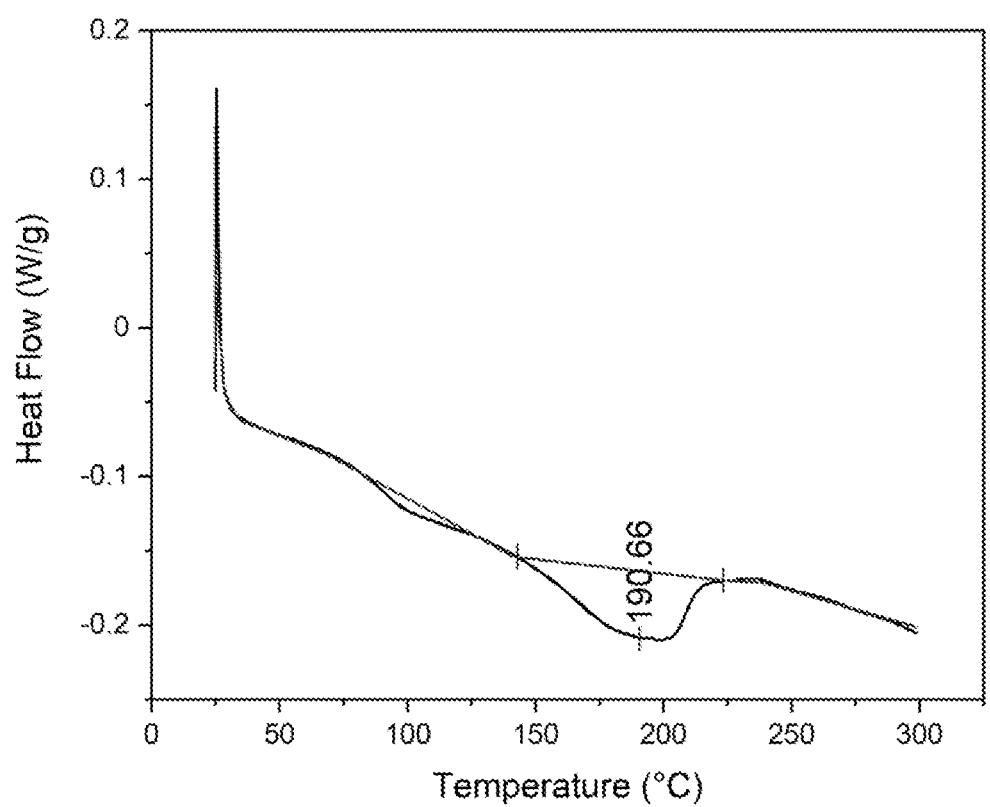
FIG. 18 show a DSC thermogram for an annealed BC-PVA hydrogel sample demonstrating how the peak was integrated.

The calculation for how much of the PVA was crystallized, i.e., the degree of crystallinity, was performed. After the DSC thermogram was acquired, the area under the melting peak over the range 140-220° C. (as shown in FIG. 18) was integrated to obtain a value with units of J·°C.·S$^{-1}$·g$^{-1}$. This number was then divided by the heating rate (0.17° C.·S$^{-1}$) to obtain ΔH (J·g$^{-1}$). The crystallinity of PVA ($X_{PVA}$), was then calculated by dividing ΔH for the sample by the heat required for melting a 100% crystalline PVA sample, (ΔHc=138.6 J/g) and the weight fraction of PVA in the sample, $w_{PVA}$:

$$X_{PVA} = \frac{\Delta H}{w_{PVA} \times \Delta H_c}$$

The weight of approximately 1 g of hydrated hydrogel was measured before drying at for 24 hours. The weight of the dehydrated sample was then measured. The weight after dehydration was divided by the weight before dehydration to determine the solid weight fraction of the hydrogel sample.

Figures 16A, 16B:
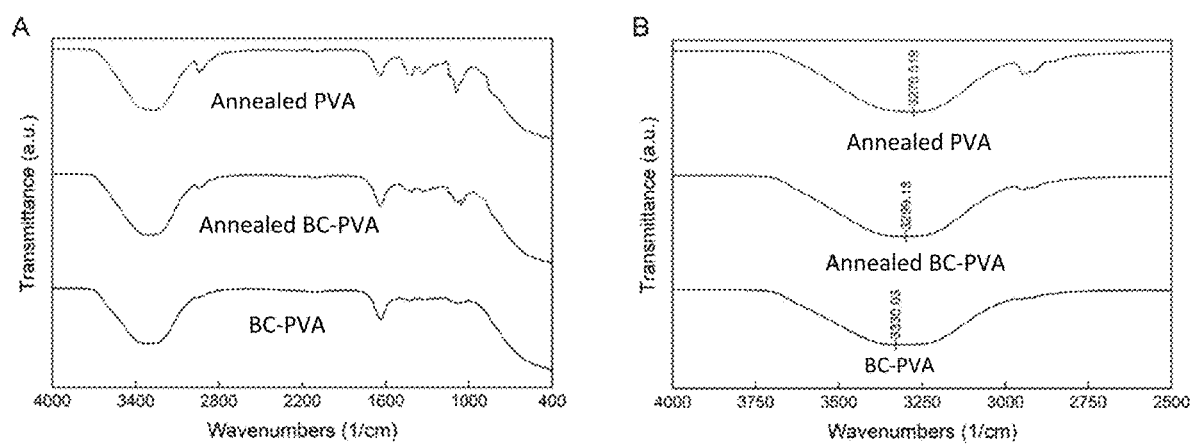
FIG. 16A shows an FTIR spectra of BC-PVA, annealed BC-PVA and annealed PVA hydrogels.
FIG. 16B shows a zoomed-in region highlighting the shift of the hydroxyl peak.

Fourier Transform Infrared (FTIR) spectroscopy was performed on hydrogel samples to analyze changes in bonding after annealing. Hydrogel samples were cut into a 1 cm by 1 cm square before testing. The tests were completed on a Thermo Scientific Nicolet iS50 FT-IR. In a typical test, the sample was held under the detector with the number of scans set to 32, resolution set to 4 (0.482 cm$^{-1}$) and format set to % transmittance. Typical FTIR spectra are shown in FIGS. 16A-16B.

The wear resistance of the hydrogels and porcine cartilage samples were determined with the pin-on-disk setup. The pin-on-disk method was used with an Anton Paar Rheometer (MR302) and a tribology accessory (SCF7). Cartilage samples were harvested from pig femurs with an osteochondral autograft transfer system (Arthrex). The femurs were purchased from a local grocery store and frozen at −78° C. before harvesting the samples. Hydrogel samples were polished with #600, #800, #1000, #1200, #1500, #2000, #2500 and #3000 sandpapers to make them smooth prior to testing. A hydrogel pin was fabricated by using the method described in section 2.8. A disk of hydrogel or porcine cartilage with a diameter of 12.7 mm was adhered with cyanoacrylate glue (Gorilla Glue Company) to the sample holder. The testing parameters were as follows: 1,000,000 rotations; angular speed: 319 rounds per minute (maximum linear velocity: 100 mm s-1); normal force: 28.26 N (pressure: 1 MPa). A pressure of 1 MPa was applied to each sample for 5 minutes before starting the test. The tests were performed in FBS. FBS is often used during wear tests to mimic the lubrication provided by synovial fluid.

After the wear test, the samples were rehydrated in FBS for 24 hours to allow the gels to recover from the applied pressure before the wear depth was measured with a High-Resolution X-ray Computed Tomography (Micro-CT) Scanner (Nikon XTH 225 ST). A 3D model of the reconstructed Micro-CT images was rendered with Avizo 9 Lite. To measure the wear depth, a slice of the 3D model was taken in the middle of the wear mark. The wear depths were measured from the images of the middle slices with ImageJ.

For calculating the COF, we determined the total friction force (F) from the torque (7) and the radius of the pin in the pin-on-disk setup (R):

$$F = \frac{3T}{2R}$$

The COF can then be calculated by:

$$COF = \frac{F}{F_N}$$

Here F N is the normal force (28.26 N). The linear velocity (v) was calculated by $$v = \omega R$$

where ω was the angular speed of the pin.

Shear testing was performed on a Test Resources 830LE63 Axial Torsion Test Machine equipped with a 100 lb. load cell. Each test was performed in a customized shear test fixture (see FIG. 13). For shearing of cartilage off bone or hydrogel off metal samples, the sample was secured in a cylindrical hole in the left side of the fixture. Spacers were added underneath the samples to precisely align the shear plane to the cartilage-bone or hydrogel-metal interface. The right side of the fixture was machined to have a complementary half-cylinder that was used to push the hydrogel or cartilage off of their substrates. A rubber spacer was placed between the sample and the right shear fixture to apply pressure during the shear test in order to minimize cleavage and peeling. A crosshead displacement rate of 2 mm min-1 was used for all the measurements.

A human-sized osteochondral implant 20 mm in diameter was fabricated. The top surface of the implant had a radius of curvature of 20 mm to match the native curvature of the femoral condyle. This implant was fabricated with 5 BC layers. A 0.25-mm-thick coating of commercially pure titanium was applied to the stem of the implant and underneath the base with a plasma spray process in order to improve integration with bone.

| Composition | Tensile Strength (MPa) | Tensile Modulus (MPa) | Compressive Strength (MPa) | Compressive Modulus (MPa) |
|---|---|---|---|---|
| Freeze-thawed BC-PVA | 11.1 | 115.3 | 55.3 | 15.0 |
| Annealed BC-PVA | 50.5 | 503.9 | 98.1 | 9.57 |
| Annealed BC-PVA-PAMPS | 22.1 | 179.0 | 60.4 | 16.5 |
| Annealed PVA | 15.6 | 24.5 | 56.7 | 12.1 |
| Freeze-thawed PVA | 0.26 | <0.14 | 14.8 | 2.41 |
| Human cartilage | 8.1-40 | 58-228 | 14-59 | 8.1-20.1 |
| BC-PVA-PAMPS | 22.6 | 227 | 23.0 | 15.2 |
| CNC-PA-PAAm | 16.5 | 232.4 | 31.1 | 65.4 |
| BC-PAAm | 40 | 114 | 5.1 | 10 |
| Polyaramid nanofiber-PVA | 5 | 9.1 | 4 | 26.5 |
| BC-gelatin | 3.8 | 21 | 5.3 | 2.9 |
| PVA-Agarose | 14.6 | 6.38 | 3.66 | 0.09 |
| PVA-HA/HAAC | 3.05 | 0.7 | 40.15 | 0.88 |
| 3D printed PCL scaffold-PVA | 4.41 | 9.53 | 3 | 1.2 |
| PVA-CS | 4.02 | 2.07 | 18 | 1.2 |

The table above shows mechanical properties of annealed BC-PVA, annealed BC-PVA-PAMPS, annealed PVA hydrogels, cartilage, and previously reported hydrogels. This table compares the properties of the anneal BC-PVA to freeze-thawed and other previous hydrogels showing a remarkable improvement in properties.

Abbreviations used in this table: BC: bacterial cellulose; PVA: Poly(vinyl alcohol); PAMPS: poly(2-acrylamido-2-methyl-1-propanesulfonic acid sodium salt); PAAm: polyacrylamide; CNC: cellulose nanocrystal, PA: phenyl acrylate; HA: hydroxyapatite, HACC: 2-hydroxypropyltrimethyl ammonium chloride chitosan, PCL: polycaprolactone, CS: chitosan. For the sake of clarity, the references in this table were limited to publications that report all four metrics, i.e., strength and modulus in tension and compression, and had a tensile and compressive strength higher than 3 MPa.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An articular cartilage implant, comprising:
an implant body having a top bearing surface;
an anchoring base; and
a cellulose-reinforced hydrogel comprising:
a cross-linked cellulose nanofiber network secured over the top bearing surface of the implant body; and an interstitial hydrogel portion infiltrated within interstitial regions of the cross-linked cellulose nanofiber network, wherein the interstitial hydrogel portion is annealed such that a crystalline content of the annealed interstitial hydrogel portion has a crystallinity of 20% or greater, wherein the cellulose-reinforced hydrogel comprises at least 20% by weight of water, wherein the cellulose-reinforced hydrogel has a tensile strength exceeding 40 MPa, wherein the cross-linked cellulose nanofiber network comprises bacterial cellulose (BC).

2. The articular cartilage implant of claim 1, wherein the interstitial hydrogel portion comprises polyvinyl alcohol (PVA).

3. The articular cartilage implant of claim 1, wherein the cross-linked cellulose nanofiber network is chemically cross-linked.

4. The articular cartilage implant of claim 1, wherein the cellulose-reinforced hydrogel has a compressive strength exceeding 59 MPa.

5. The articular cartilage implant of claim 1, wherein the cross-linked cellulose nanofiber network is secured over the top bearing surface by a clamp.

6. The articular cartilage implant of claim 5, wherein the cross-linked cellulose nanofiber network comprises one or more sheets of bacterial cellulose (BC) held over the top bearing surface by a clamp secured to a lip or rim of the top bearing surface.

7. The articular cartilage implant of claim 1, wherein the cellulose-reinforced hydrogel is attached to a metallic base of the top bearing surface with a shear strength exceeding 0.2 MPa.

8. The articular cartilage implant of claim 1, wherein the top bearing surface has a coefficient of friction (COF) that is not statistically greater than that of cartilage.

* * * * *